United States Patent
Spann et al.

(10) Patent No.: US 10,716,553 B2
(45) Date of Patent: Jul. 21, 2020

(54) SPINE SURGERY RETRACTOR SYSTEM AND RELATED METHODS

(71) Applicant: Pantheon Spinal, LLC, Austin, TX (US)

(72) Inventors: Scott Spann, Austin, TX (US); Shawn H. Culbertson, Georgetown, TX (US); Ronald R. Jordan, Leander, TX (US); David Frederick Crook, Mineola, TX (US)

(73) Assignee: Pantheon Spinal, LLC, Georgetown, TX (US)

( * ) Notice: Subject to any disclaimer, the term of this patent is extended or adjusted under 35 U.S.C. 154(b) by 0 days.

(21) Appl. No.: 15/956,455

(22) Filed: Apr. 18, 2018

(65) Prior Publication Data
US 2018/0303473 A1 Oct. 25, 2018

Related U.S. Application Data

(60) Provisional application No. 62/487,329, filed on Apr. 19, 2017, provisional application No. 62/487,349, filed on Apr. 19, 2017.

(51) Int. Cl.
*A61B 17/02* (2006.01)
*A61B 17/84* (2006.01)

(52) U.S. Cl.
CPC .......... *A61B 17/0206* (2013.01); *A61B 17/02* (2013.01); *A61B 17/848* (2013.01); *A61B 2017/0256* (2013.01)

(58) Field of Classification Search
CPC ........................................... A61B 17/02–0293
See application file for complete search history.

(56) References Cited

U.S. PATENT DOCUMENTS

| 1,706,500 A | 3/1929 | Smith |
| 4,934,352 A | 6/1990 | Sullivan |

(Continued)

FOREIGN PATENT DOCUMENTS

| WO | WO2005030318 | 4/2005 |
| WO | WO2006042241 | 4/2006 |

(Continued)

OTHER PUBLICATIONS

Extended European Search Report for European Patent Application No. EP09835860, date of completion: Feb. 7, 2013 (6 pages).

(Continued)

*Primary Examiner* — Nicholas J Plionis
(74) *Attorney, Agent, or Firm* — Fish & Richardson P.C.

(57) ABSTRACT

A retractor system and related methods for use in spinal surgery procedures, including but not limited to fusing or repairing damaged or deteriorated intervertebral discs or vertebral bodies in the lower lumbar levels. The retractor system includes a plurality of blade assemblies coupled to a handle assembly, wherein each of the blade assemblies may be independently adjusted (e.g. length blade and/or blade angulation and/or blade rotation relative to the handle assembly) to provide unprecedented customization of an operative corridor extending to the surgical target site of the patient such that any number of spinal surgery procedures may be undertaken by a surgeon, including but not limited to spinal fusion procedures at the L5-S1 disc space.

20 Claims, 29 Drawing Sheets

(56) References Cited

U.S. PATENT DOCUMENTS

| | | | |
|---|---|---|---|
| 5,297,538 A | 3/1994 | Daniel | |
| 5,337,736 A | 8/1994 | Reddy | |
| 5,352,219 A | 10/1994 | Reddy | |
| 5,514,180 A | 5/1996 | Heggeness et al. | |
| 5,599,279 A | 2/1997 | Slotman et al. | |
| 5,609,635 A | 3/1997 | Michelson | |
| 5,772,661 A | 6/1998 | Michelson | |
| 5,776,199 A | 7/1998 | Michelson | |
| 5,860,973 A | 1/1999 | Michelson | |
| 5,895,352 A | 4/1999 | Kleiner | |
| 5,931,777 A | 8/1999 | Sava | |
| 5,944,658 A | 8/1999 | Koros et al. | |
| 5,984,922 A | 11/1999 | McKay | |
| 6,030,401 A | 2/2000 | Marino | |
| 6,042,540 A | 3/2000 | Johnson et al. | |
| 6,080,155 A | 6/2000 | Michelson | |
| 6,096,026 A | 8/2000 | Schultz | |
| 6,139,493 A | 10/2000 | Koros et al. | |
| 6,143,032 A | 11/2000 | Schafer et al. | |
| 6,159,215 A | 12/2000 | Urbahns et al. | |
| 6,183,517 B1 | 2/2001 | Suddaby | |
| 6,221,082 B1 | 4/2001 | Marino et al. | |
| 6,224,603 B1 | 5/2001 | Marino | |
| 6,245,108 B1 | 6/2001 | Biscup | |
| 6,251,140 B1 | 6/2001 | Marino et al. | |
| 6,266,394 B1 | 7/2001 | Marino | |
| 6,280,447 B1 | 8/2001 | Marino et al. | |
| 6,290,724 B1 | 9/2001 | Marino | |
| 6,312,443 B1 | 11/2001 | Stone | |
| 6,368,325 B1 | 4/2002 | McKinley et al. | |
| 6,387,070 B1 | 5/2002 | Marino et al. | |
| 6,387,130 B1 | 5/2002 | Stone et al. | |
| 6,416,465 B2 | 7/2002 | Brau | |
| 6,466,817 B1 | 10/2002 | Kaula et al. | |
| 6,478,805 B1 | 11/2002 | Marino et al. | |
| 6,485,518 B1 | 11/2002 | Cornwall et al. | |
| 6,491,626 B1 | 12/2002 | Stone et al. | |
| 6,500,128 B2 | 12/2002 | Marino | |
| 6,519,319 B1 | 2/2003 | Marino et al. | |
| 6,533,797 B1 | 3/2003 | Stone et al. | |
| 6,540,747 B1 | 4/2003 | Marino | |
| 6,564,078 B1 | 5/2003 | Marino et al. | |
| 6,723,043 B2 | 4/2004 | Kleeman et al. | |
| 6,764,452 B1 | 7/2004 | Gillespie et al. | |
| 6,802,844 B2 | 10/2004 | Ferree | |
| 6,852,126 B2 | 2/2005 | Ahlgren | |
| 6,887,248 B2 | 5/2005 | McKinley et al. | |
| 6,923,814 B1 | 8/2005 | Hildebrand et al. | |
| 6,945,973 B2 | 9/2005 | Bray | |
| 6,964,674 B1 | 11/2005 | Matsuura et al. | |
| 7,025,769 B1 | 4/2006 | Ferree | |
| 7,050,848 B2 | 5/2006 | Hoey et al. | |
| 7,115,132 B2 | 10/2006 | Errico et al. | |
| 7,125,380 B2 | 10/2006 | Yager | |
| 7,156,875 B2 | 1/2007 | Michelson | |
| 7,162,850 B2 | 1/2007 | Marino et al. | |
| 7,166,113 B2 | 1/2007 | Arambula et al. | |
| 7,169,182 B2 | 1/2007 | Errico et al. | |
| 7,177,677 B2 | 2/2007 | Kaula et al. | |
| 7,207,949 B2 | 4/2007 | Miles et al. | |
| 7,207,991 B2 | 4/2007 | Michelson | |
| 7,235,081 B2 | 6/2007 | Errico et al. | |
| 7,235,082 B2 | 6/2007 | Bartish et al. | |
| 7,261,688 B2 | 8/2007 | Smith et al. | |
| 7,288,093 B2 | 10/2007 | Michelson | |
| 7,320,688 B2 | 1/2008 | Foley et al. | |
| 7,326,216 B2 | 2/2008 | Bertagnoli et al. | |
| 7,341,587 B2 | 3/2008 | Molz et al. | |
| 7,341,590 B2 | 3/2008 | Ferree | |
| 7,361,193 B2 | 4/2008 | Frey et al. | |
| 7,452,359 B1 | 11/2008 | Michelson | |
| 7,455,692 B2 | 11/2008 | Michelson | |
| 7,462,195 B1 | 12/2008 | Michelson | |
| 7,470,236 B1 | 12/2008 | Kelleher et al. | |
| 7,473,222 B2 | 1/2009 | Dewey et al. | |
| 7,476,252 B2 | 1/2009 | Foley | |
| 7,481,812 B2 | 1/2009 | Frey et al. | |
| 7,485,146 B1 | 2/2009 | Crook et al. | |
| 7,491,205 B1 | 2/2009 | Michelson | |
| 7,503,933 B2 | 3/2009 | Michelson | |
| 7,513,869 B2 | 4/2009 | Branch et al. | |
| 7,522,953 B2 | 4/2009 | Kaula et al. | |
| 7,524,285 B2 | 4/2009 | Branch et al. | |
| 7,527,649 B1 | 5/2009 | Blain | |
| 1,313,390 A1 | 12/2009 | Spann | |
| 7,819,801 B2 | 10/2010 | Miles et al. | |
| 8,394,144 B2 | 3/2013 | Zehavi et al. | |
| 8,506,629 B2 | 8/2013 | Weiland | |
| 9,451,940 B2 | 9/2016 | Spann | |
| 2001/0034535 A1 | 10/2001 | Schultz | |
| 2002/0013514 A1 | 1/2002 | Brau | |
| 2002/0120336 A1 | 8/2002 | Santilli | |
| 2002/0165612 A1 | 11/2002 | Gerber et al. | |
| 2003/0060687 A1 | 3/2003 | Kleeman et al. | |
| 2003/0233147 A1 | 12/2003 | Nicholson et al. | |
| 2004/0024291 A1 | 2/2004 | Zinkel | |
| 2004/0106927 A1 | 6/2004 | Ruffner et al. | |
| 2004/0117020 A1 | 6/2004 | Frey et al. | |
| 2004/0176665 A1 | 9/2004 | Branch et al. | |
| 2005/0043796 A1 | 2/2005 | Grant et al. | |
| 2005/0071009 A1 | 3/2005 | Muhanna et al. | |
| 2005/0080320 A1* | 4/2005 | Lee | A61B 17/02 600/214 |
| 2005/0149035 A1 | 7/2005 | Pimenta et al. | |
| 2006/0069315 A1 | 3/2006 | Miles et al. | |
| 2006/0195017 A1 | 8/2006 | Shluzas et al. | |
| 2006/0224044 A1 | 10/2006 | Marchek et al. | |
| 2006/0229627 A1 | 10/2006 | Hunt et al. | |
| 2006/0235426 A1 | 10/2006 | Lim et al. | |
| 2007/0055109 A1 | 3/2007 | Bass et al. | |
| 2007/0093850 A1 | 4/2007 | Harris et al. | |
| 2007/0100212 A1* | 5/2007 | Pimenta | A61B 5/0488 600/210 |
| 2007/0156026 A1 | 7/2007 | Frasier et al. | |
| 2007/0173941 A1 | 7/2007 | Allard | |
| 2007/0179611 A1 | 8/2007 | DePoto et al. | |
| 2007/0203580 A1 | 8/2007 | Yeh | |
| 2007/0208227 A1 | 9/2007 | Smith et al. | |
| 2007/0213826 A1 | 9/2007 | Smith et al. | |
| 2007/0225726 A1 | 9/2007 | Dye et al. | |
| 2007/0225808 A1 | 9/2007 | Warnick | |
| 2007/0255415 A1 | 11/2007 | Edie et al. | |
| 2007/0282449 A1 | 12/2007 | deVilliers | |
| 2008/0021285 A1 | 1/2008 | Drzyzga et al. | |
| 2008/0058606 A1 | 3/2008 | Miles et al. | |
| 2008/0065082 A1 | 3/2008 | Chang et al. | |
| 2008/0065219 A1 | 3/2008 | Dye | |
| 2008/0077241 A1 | 3/2008 | Nguyen | |
| 2008/0077247 A1 | 3/2008 | Murillo et al. | |
| 2008/0091211 A1 | 4/2008 | Gately | |
| 2008/0097164 A1 | 4/2008 | Miles et al. | |
| 2008/0119851 A1 | 5/2008 | Shelokov | |
| 2008/0140085 A1 | 6/2008 | Gately et al. | |
| 2008/0183046 A1 | 7/2008 | Boucher et al. | |
| 2008/0215153 A1 | 9/2008 | Butterman et al. | |
| 2008/0221694 A1 | 9/2008 | Warnick et al. | |
| 2008/0300688 A1 | 12/2008 | Cannon et al. | |
| 2009/0030423 A1 | 1/2009 | Puno | |
| 2009/0036746 A1* | 2/2009 | Blackwell | A61B 17/0206 600/219 |
| 2009/0043345 A1 | 2/2009 | Mathews | |
| 2009/0099660 A1 | 4/2009 | Scifert et al. | |
| 2009/0259108 A1 | 10/2009 | Miles et al. | |
| 2010/0094422 A1 | 4/2010 | Hansell et al. | |
| 2010/0178100 A1* | 7/2010 | Fricke | F16C 11/106 403/90 |
| 2012/0010472 A1 | 1/2012 | Spann | |
| 2012/0010715 A1 | 1/2012 | Spann | |
| 2012/0010716 A1 | 1/2012 | Spann | |
| 2012/0010717 A1 | 1/2012 | Spann | |
| 2012/0035730 A1 | 2/2012 | Spann | |
| 2012/0245431 A1* | 9/2012 | Baudouin | A61B 17/0206 600/213 |

(56) References Cited

U.S. PATENT DOCUMENTS

| | | | | |
|---|---|---|---|---|
| 2012/0296171 | A1* | 11/2012 | Lovell | A61B 17/0206 600/213 |
| 2013/0190575 | A1* | 7/2013 | Mast | A61B 17/7079 600/215 |
| 2014/0350347 | A1* | 11/2014 | Karpowicz | A61B 17/0206 600/215 |
| 2015/0313585 | A1* | 11/2015 | Abidin | A61B 17/0206 600/213 |
| 2016/0081681 | A1* | 3/2016 | Waugh | A61B 17/0206 606/86 A |
| 2017/0231614 | A1* | 8/2017 | Vogel | A61B 17/0206 600/224 |

FOREIGN PATENT DOCUMENTS

| | | |
|---|---|---|
| WO | WO2007016247 | 2/2007 |
| WO | WO2010075555 | 1/2010 |

OTHER PUBLICATIONS

Gumbs et al., "Open Anterior Approaches for Lumbar Spine Procedures," The American Journal of Surgery 194:98-102, 2007.

Gumbs et al., "The Open Anterior Paramedian Retroperitoneal Approach for Spine Procedures," Arch Surg 140:339-343, Apr. 2005.

International Search Report and Written Opinion for PCT/US2009/069476, dated Aug. 17, 2010. (5 pages).

International Preliminary Report on Patentability for PCT/US2009/069476, dated Jun. 29, 2011, 7 pages.

Patent Examination Report no. 1 for Australian Patent Application No. 2009329873, dated Mar. 7, 2014. (4 pages).

USPTO Advisory Action for U.S. Appl. No. 13/133,909, dated Jul. 2, 2013.

USPTO Advisory Action for U.S. Appl. No. 13/239,042, dated Feb. 6, 2014.

USPTO Advisory Action for U.S. Appl. No. 13/239,053, dated Feb. 13, 2014.

USPTO Final Office Action for U.S. Appl. No. 13/133,909, dated Mar. 20, 2013.

USPTO Final Office Action for U.S. Appl. No. 13/239,014, dated Sep. 14, 2015.

USPTO Final Office Action for U.S. Appl. No. 13/239,024, dated Jun. 17, 2014.

USPTO Final Office Action for U.S. Appl. No. 13/239,014, dated Oct. 30, 2013.

USPTO Final Office Action for U.S. Appl. No. 13/239,024, dated Jul. 19, 2013.

USPTO Final Office Action for U.S. Appl. No. 13/239,042, dated Oct. 30, 2013.

USPTO Final Office Action for U.S. Appl. No. 13/239,053, dated Oct. 18, 2013.

USPTO Interview Summary for U.S. Appl. No. 13/133,909, dated Dec. 26, 2013.

USPTO Interview Summary for U.S. Appl. No. 13/239,014, dated Dec. 24, 2013.

USPTO Interview Summary for U.S. Appl. No. 13/239,014, dated Dec. 31, 2015.

USPTO Interview Summary for U.S. Appl. No. 13/239,014, dated May 6, 2015.

USPTO Interview Summary for U.S. Appl. No. 13/239,024, dated Dec. 30, 2013.

USPTO Interview Summary for U.S. Appl. No. 13/239,042, dated Dec. 27, 2013.

USPTO Interview Summary for U.S. Appl. No. 13/239,053, dated Dec. 26, 2013.

USPTO Non-Final Office Action for U.S. Appl. No. 13/133,909, dated Jul. 13, 2012.

USPTO Non-Final Office Action for U.S. Appl. No. 13/133,909, dated Sep. 10, 2014.

USPTO Non-Final Office Action for U.S. Appl. No. 13/239,014, dated Dec. 4, 2014.

USPTO Non-Final Office Action for U.S. Appl. No. 13/239,014, dated Feb. 21, 2013.

USPTO Non-Final Office Action for U.S. Appl. No. 13/239,024, dated Dec. 20, 2012.

USPTO Non-Final Office Action for U.S. Appl. No. 13/239,024, dated Jan. 28, 2014.

USPTO Non-Final Office Action for U.S. Appl. No. 13/239,024, dated Nov. 28, 2014.

USPTO Non-Final Office Action for U.S. Appl. No. 13/239,042, dated Dec. 4, 2014.

USPTO Non-Final Office Action for U.S. Appl. No. 13/239,042, dated Mar. 6, 2013.

USPTO Non-Final Office Action for U.S. Appl. No. 13/239,053, dated Nov. 6, 2014.

USPTO Non-Final Office Action for U.S. Appl. No. 13/239,053, dated Jan. 29, 2013.

USPTO Requirement for Restriction/Election for U.S. Appl. No. 13/239,053, dated Nov. 2, 2012.

* cited by examiner

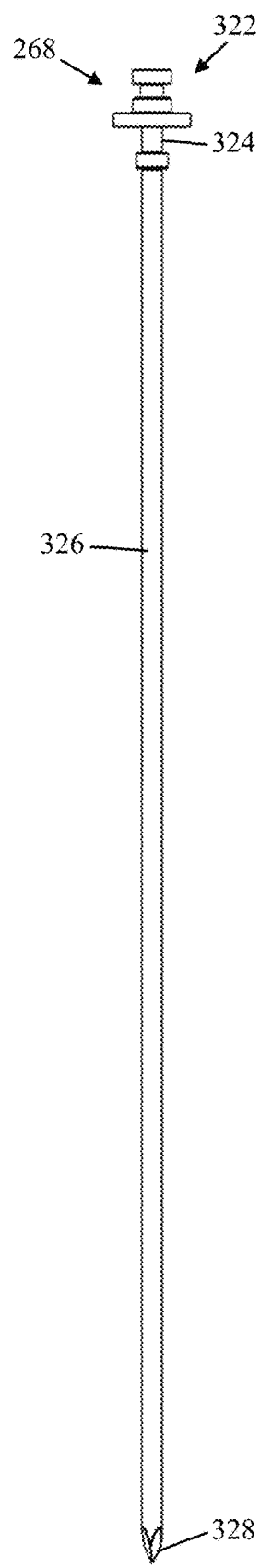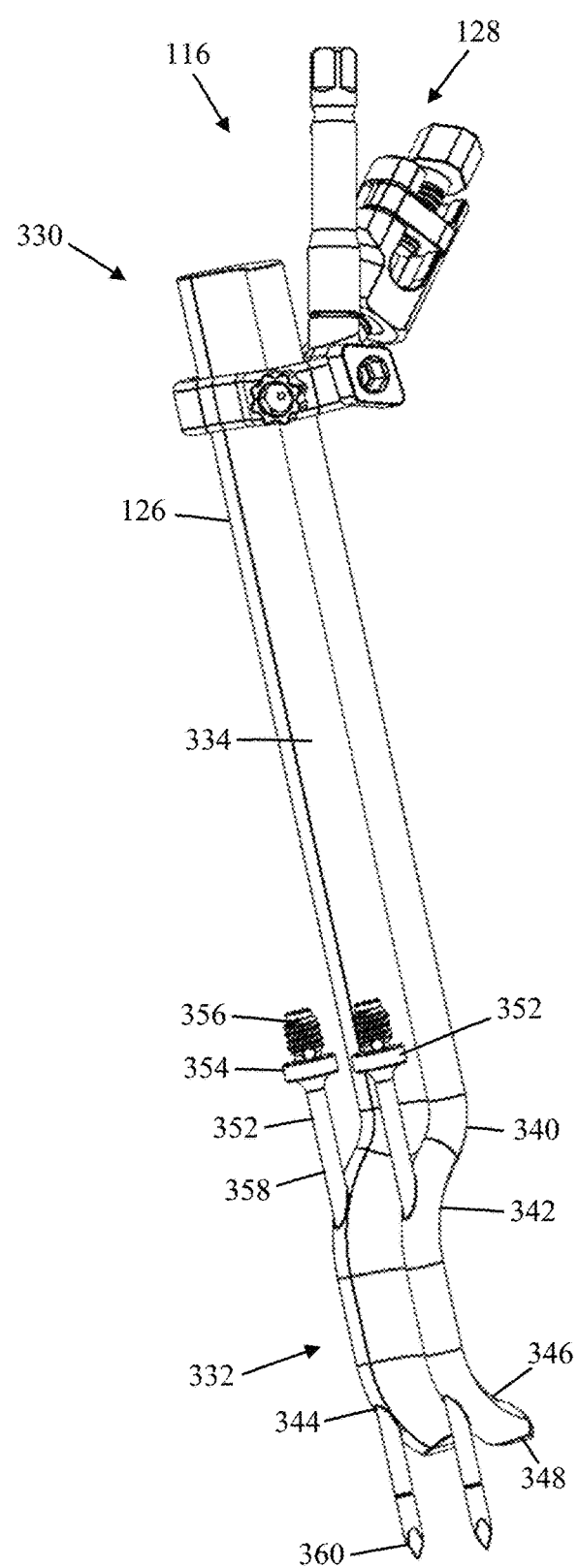
Fig. 23
Fig. 24

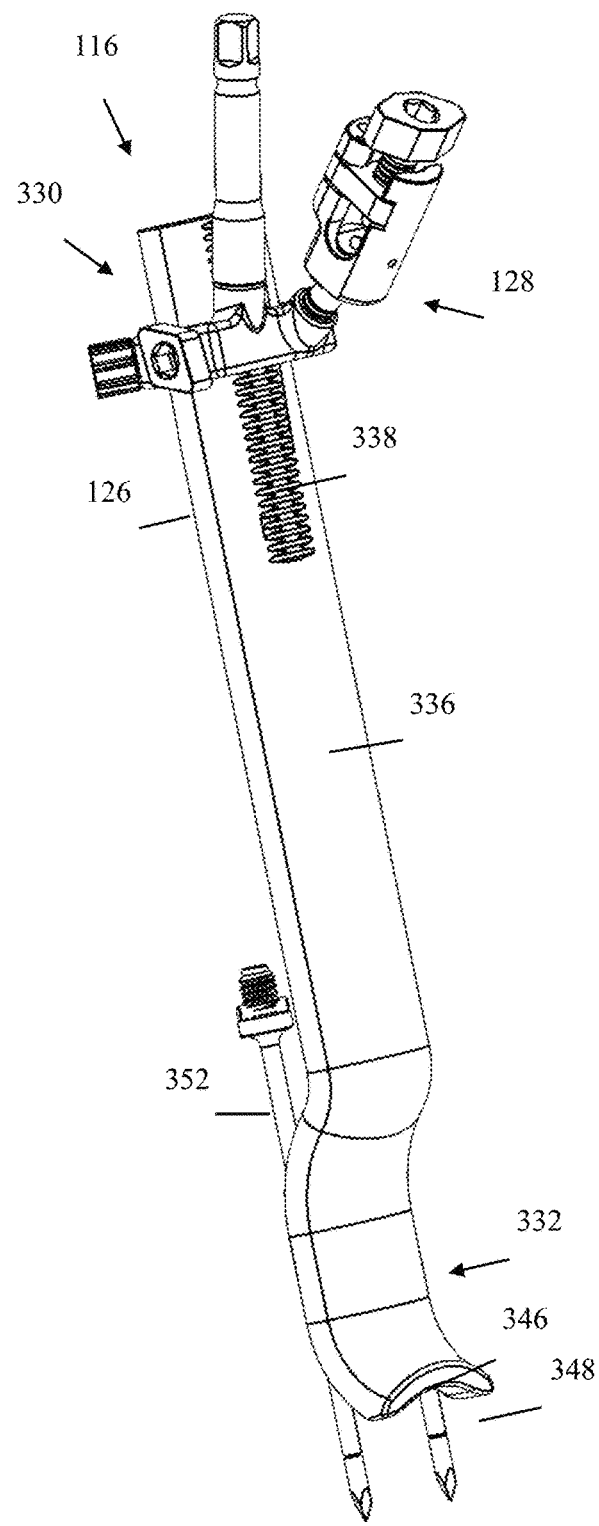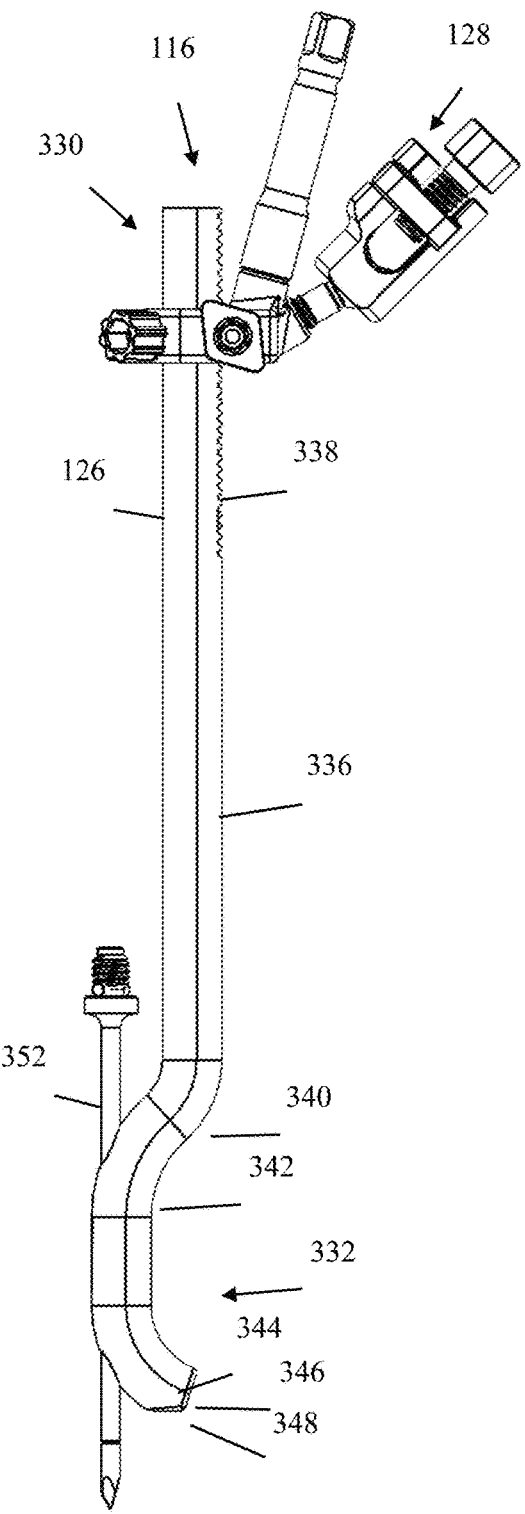
Fig. 25
Fig. 26

SPINE SURGERY RETRACTOR SYSTEM AND RELATED METHODS

CROSS-REFERENCES TO RELATED APPLICATIONS

The present application is a non-provisional application claiming the benefit of priority under 35 U.S.C. 119(e) from commonly owned and U.S. Provisional Application Ser. No. 62/487,349, filed on Apr. 19, 2017, and U.S. Provisional Application Ser. No. 62/487,329, filed on Apr. 19, 2017, and are entitled "Spine Surgery Retractor System and Related Methods," the entire contents of which are hereby incorporated by reference into this disclosure as if set forth fully herein.

FIELD

The present disclosure relates generally to the field of surgery and, more specifically, a retractor system for use in spine surgery procedures, including but not limited to repairing damaged or deteriorated vertebrae at the lower lumbar levels, such as in the L5-S1 intervertebral space.

BACKGROUND

The vertebral column is the central pillar of the body. It is a generally flexible column that bears tensile and compressive loads, permits bending motions, and provides an attachment site for ribs, muscles and other structures. The vertebral column includes irregular bones called vertebrae that are separated by fibrocartilaginous structures known as intervertebral discs. There are seven vertebral, twelve thoracic, five lumbar, five sacral, and four coccygeal vertebrae. A typical vertebra consists of a rounded anterior body and a posterior vertebral arch that together form a protective structure around the vertebral canal that contains the spinal cord.

The intervertebral discs can be damaged or undergo degeneration, which often results in painful and sometimes debilitating nerve impingement syndromes. It is sometimes necessary to surgically replace the native disc with prosthetic disc implants to relieve the pain, restore the functional mechanics of the vertebral column, and promote fusion between adjacent vertebral bodies. Procedures such as total disc arthroplasty (disc replacement) have used a direct anterior approach orthogonal to the midline of the vertebral body, but such procedures require unfettered anterior spinal exposure for precise midline placement of the prosthetic disc. The major vascular structures that run along the anterior spine must be mobilized to achieve this exposure, which typically requires the assistance of a vascular surgeon. The procedure also causes significant surgical disruption of the anterior annular element around the disc.

Bertagnoli has described an anterolateral transpsoatic approach (ALPA) for implantation of prosthetic disc replacement devices. The patient is positioned in a supine position on the operating table, with the arms in abduction. The target disc level is localized through bi-planar fluoroscopy, and an inflatable bladder is placed beneath the level of interest to permit additional lordosis. An anterolateral incision is made on the left side for access to lumbar intervertebral spaces, while the incision is made on the right side for access to L5-S1. The fascia of the external oblique muscle is opened along the direction of its fibers and the muscle is split. The retroperitoneal space is entered and the peritoneal sac mobilized away from the overlying fascia to develop an operative pathway along the anterior aspect of the psoas muscle to the lateral aspect of the intervertebral space. The target zone for annulotomy is from the one o'clock to three o'clock position above the L5-S1 level, which leaves the anterior longitudinal ligament intact and avoids mobilizing the iliac vessels. At the L5-S1 level the target annulotomy zone is from the eight o'clock to ten o'clock position with mobilization of the iliac vessel toward the midline. Injury to the left iliac vessel is an unfortunate complication of such procedures. Additional information about anterolateral approaches to spinal surgery at the L4-L5 level is found in Bertognali et al, U.S. Pat. No. 7,326,216.

A minimally invasive procedure promoted by Nuvasive, Inc. uses a direct lateral, retroperitoneal approach to access the intervertebral discs above the L5-S1 level with minimal muscular disruption. The patient is placed in a lateral decubitus position and the direct lateral incision is made in the axillary line. Another incision is made posterior to the lateral border of the erector spinae muscle, and finger dissection is conducted through this opening to the retroperitoneal space. The index finger of the surgeon sweeps the peritoneum anteriorly and palpates the psoas muscle. A dilator instrument is then introduced through the direct lateral incision and the index finger then guides the dilator instrument to the psoas muscle. The fibers of the psoas muscle are then split using blunt dissection and EMG monitoring to minimize damage to the nerves of the lumbar plexus that run through the posterior psoas muscle. A tissue distraction and tissue retraction assembly are then used to help establish an operative corridor to the direct lateral aspect of the intervertebral space at about the 3 o'clock position, as shown in U.S. Pat. No. 7,207,949. The direct lateral retroperitoneal approach to the L5-S1 space has not been possible because the anterior superior iliac spine obstructs a direct lateral approach to the L5-S1 intervertebral space. Hence approaches to the L5-S1 space typically use a standard anterior approach. For a laterally positioned patient, an extremely large sigmoidal incision has been required, with subsequent reflection of all the overlying musculature to expose the L5-S1 space.

It would therefore be useful to provide a minimally invasive approach to the L5-S1 space that minimizes injury to the blood vessels and nerves around the vertebral bodies. It would also be helpful to perform such a procedure in a manner that minimizes retroperitoneal scarring and damage to other body structures. Minimally invasive surgical approaches to the intervertebral spaces in the past have also been limited by the need to insert the prosthetic disc implant either into the front portion, posterior portion, or the side of the disc space to achieve stable placement of the prosthetic implant. It would therefore be useful to have a procedure that could avoid such a limitation at any vertebral level.

The present disclosure is directed to a retractor system specifically designed and optimized to address the various unmet needs associated with performing spine surgery procedures at the L5-S1 disc space.

SUMMARY

A retractor system is disclosed that addresses the previously unmet needs through the combination of a plurality of blade assemblies coupled to a handle assembly, wherein each of the blade assemblies is configured to provide unprecedented customization of an operative corridor extending to the surgical target site of the patient such that any number of spinal surgery procedures may be undertaken by a surgeon, including but not limited to spinal fusion procedures at the L5-S1 disc space. The retractor system may be used according to the teachings of U.S. Pat. No. 9,451,940 (invented by Dr. Scott Spann of Austin Tx., inventor of the present application), which is attached hereto as Exhibit A and forms part of this provisional patent application.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIG. 23 is a front plan view of an example of an anchor pin forming part of the first retractor blade assembly of FIG. 19;

FIG. 24 is a front perspective view of a blade holder assembly coupled with a second retractor blade, forming part of the surgical retractor system of FIG. 5 according to an aspect of the disclosure;

FIG. 25 is a rear perspective view of the blade holder assembly coupled with the second retractor blade of FIG. 24;

FIG. 26 is a side plan view of the blade holder assembly coupled with the second retractor blade of FIG. 24;

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical retractor system disclosed herein boasts a variety of inventive features and components that warrant patent protection, both individually and in combination.

Figure 1:
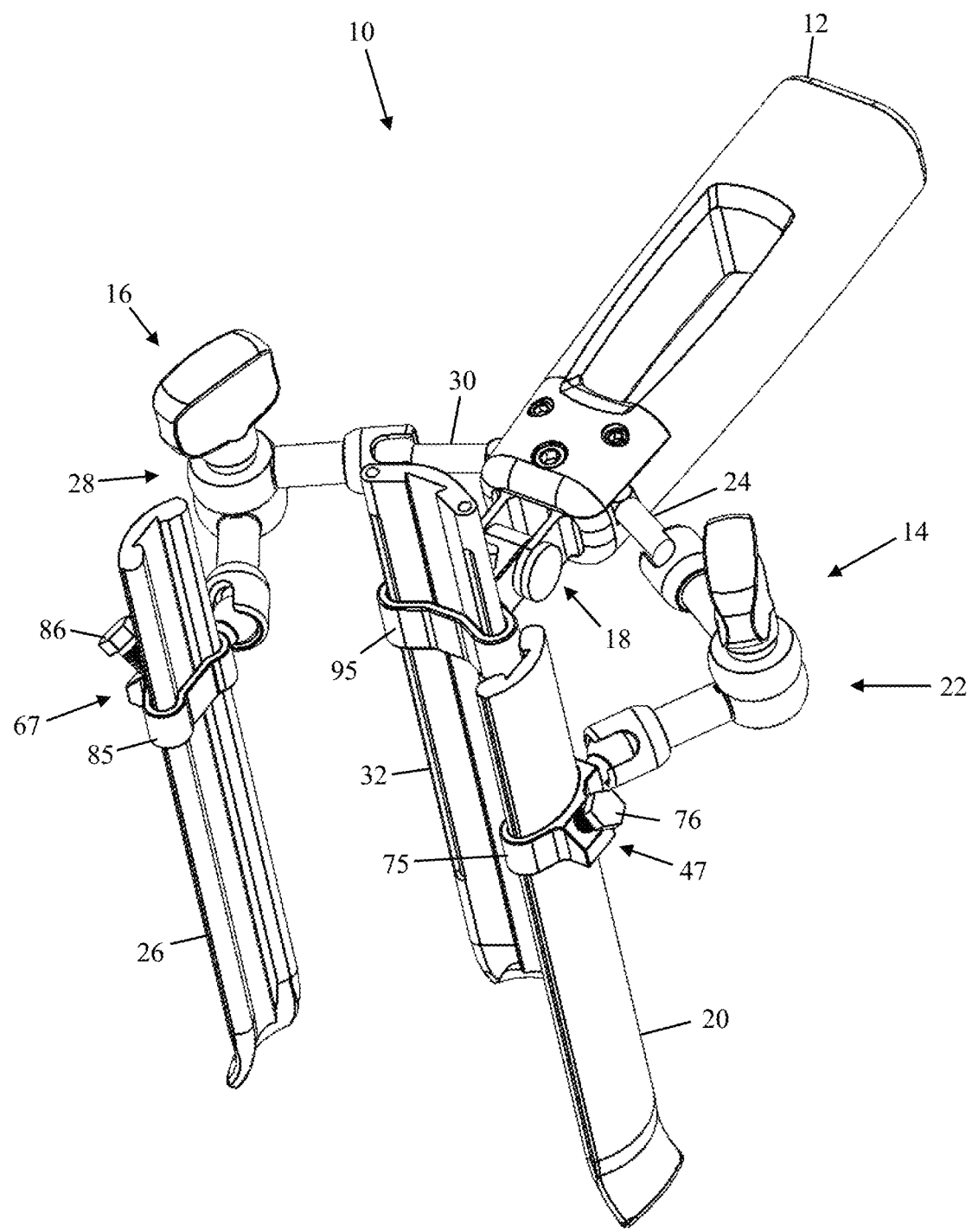
FIG. 1 is an elevated perspective view of one example of a surgical retractor system with retractor blades in a generally open configuration according to one aspect of the disclosure.
Figure 2:
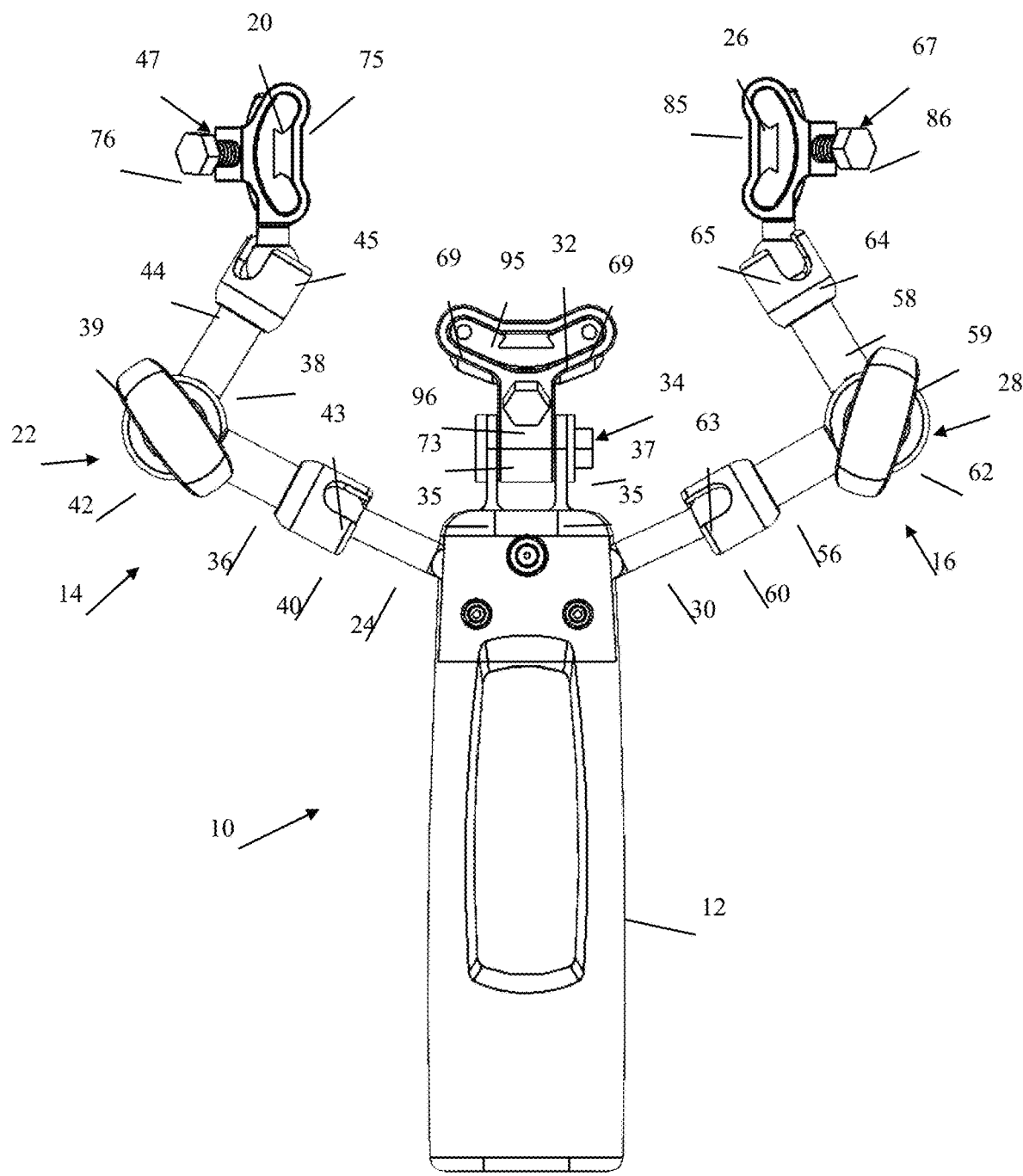
FIG. 2 is a top plan view of the surgical retractor system of FIG. 1.
Figure 3:
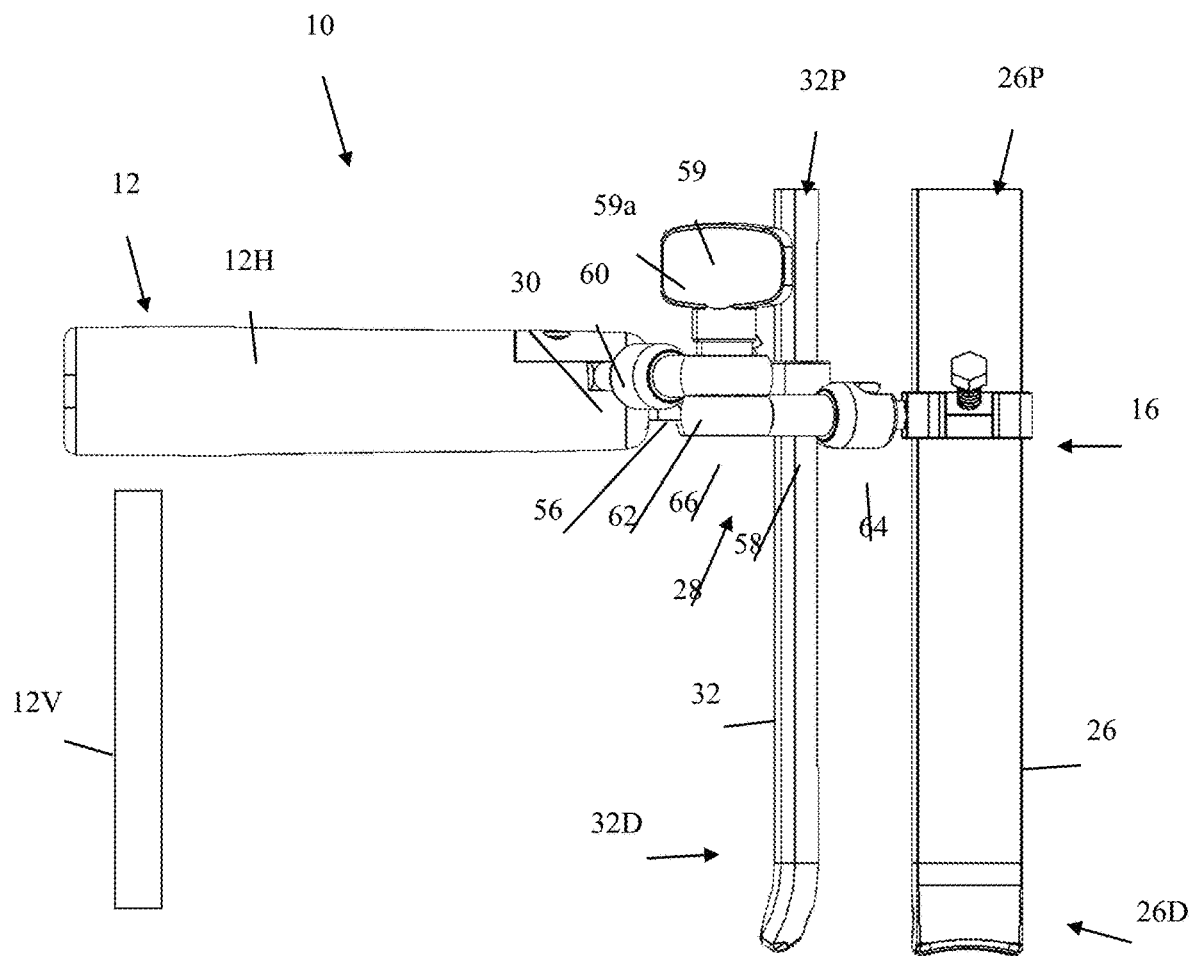
FIG. 3 is a side plan view of the surgical retractor system of FIG. 1.
Figure 4:
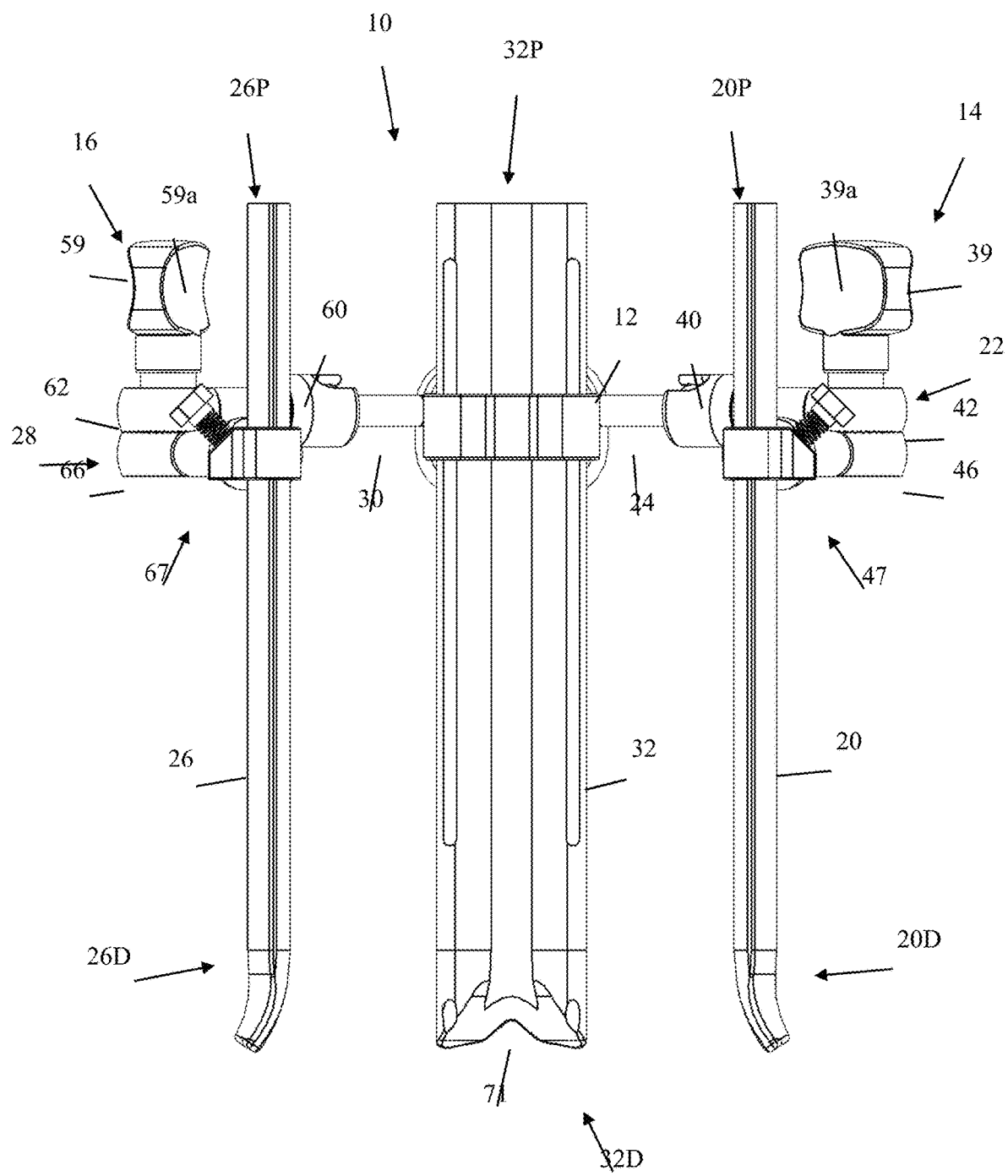
FIG. 4 is a front plan view of the surgical retractor system of FIG. 1.
Figure 5:
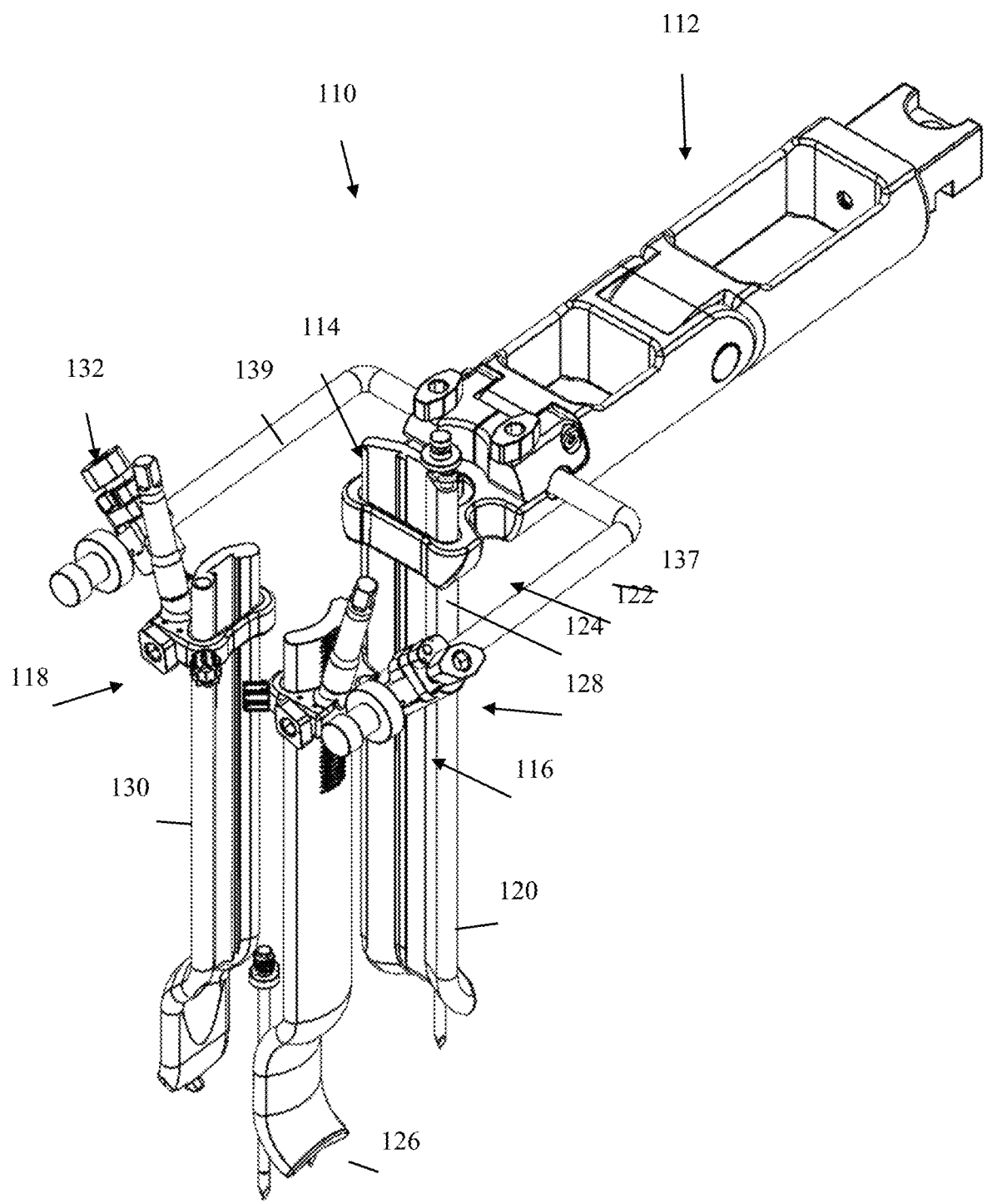
FIG. 5 is an elevated perspective view of another example of a surgical retractor system with retractor blades in a generally closed configuration according to one aspect of the disclosure.
Figure 6:
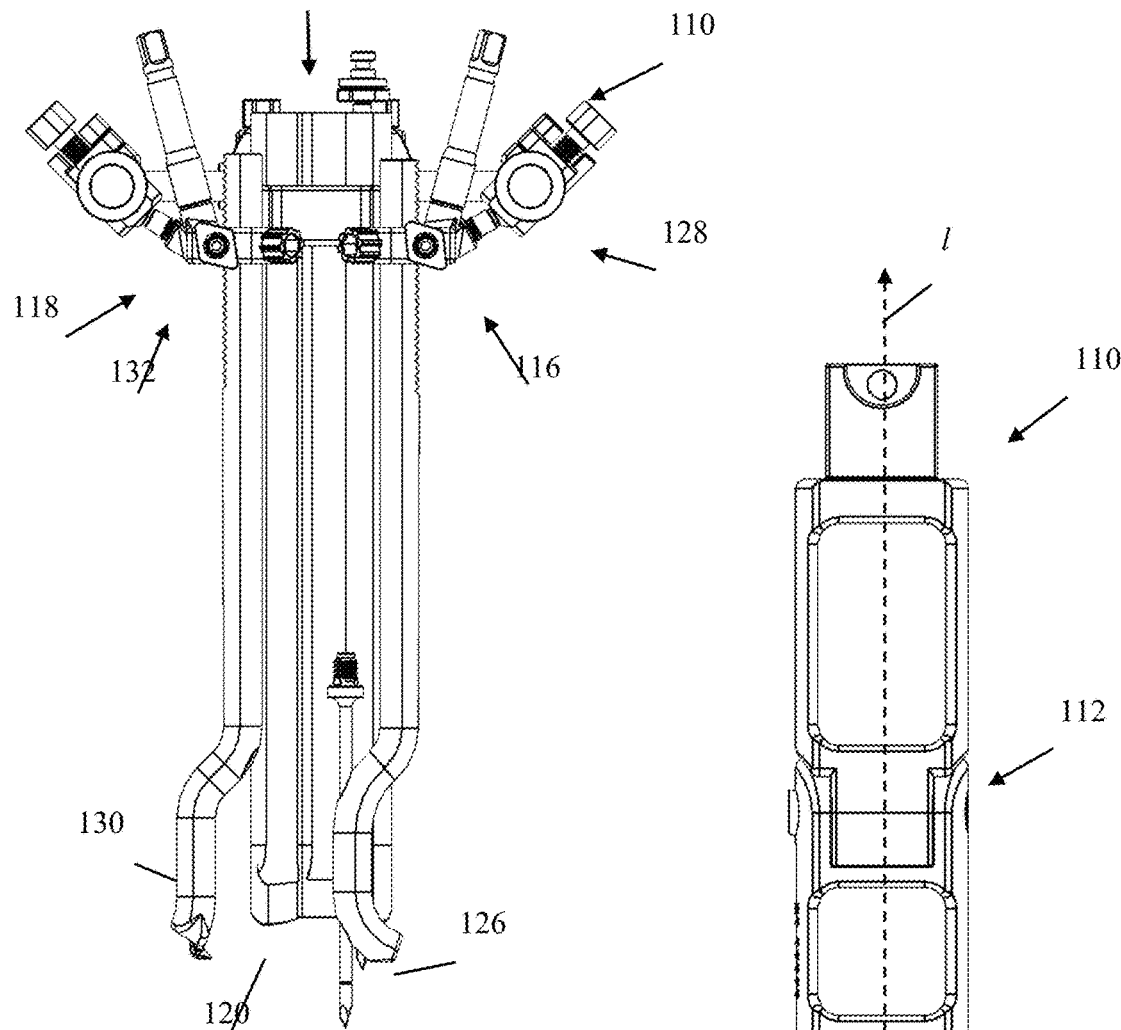
FIG. 6 is a front view plan of the surgical retractor system of FIG. 5.
Figure 7:
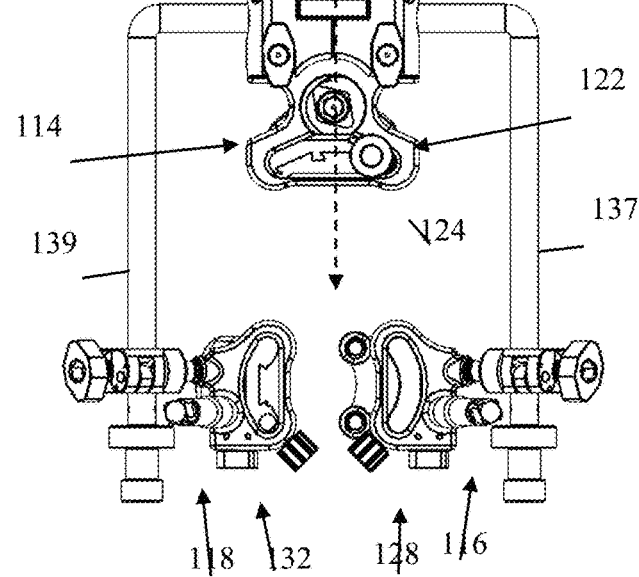
FIG. 7 is a top plan view of the surgical retractor system of FIG. 5.
Figure 8:
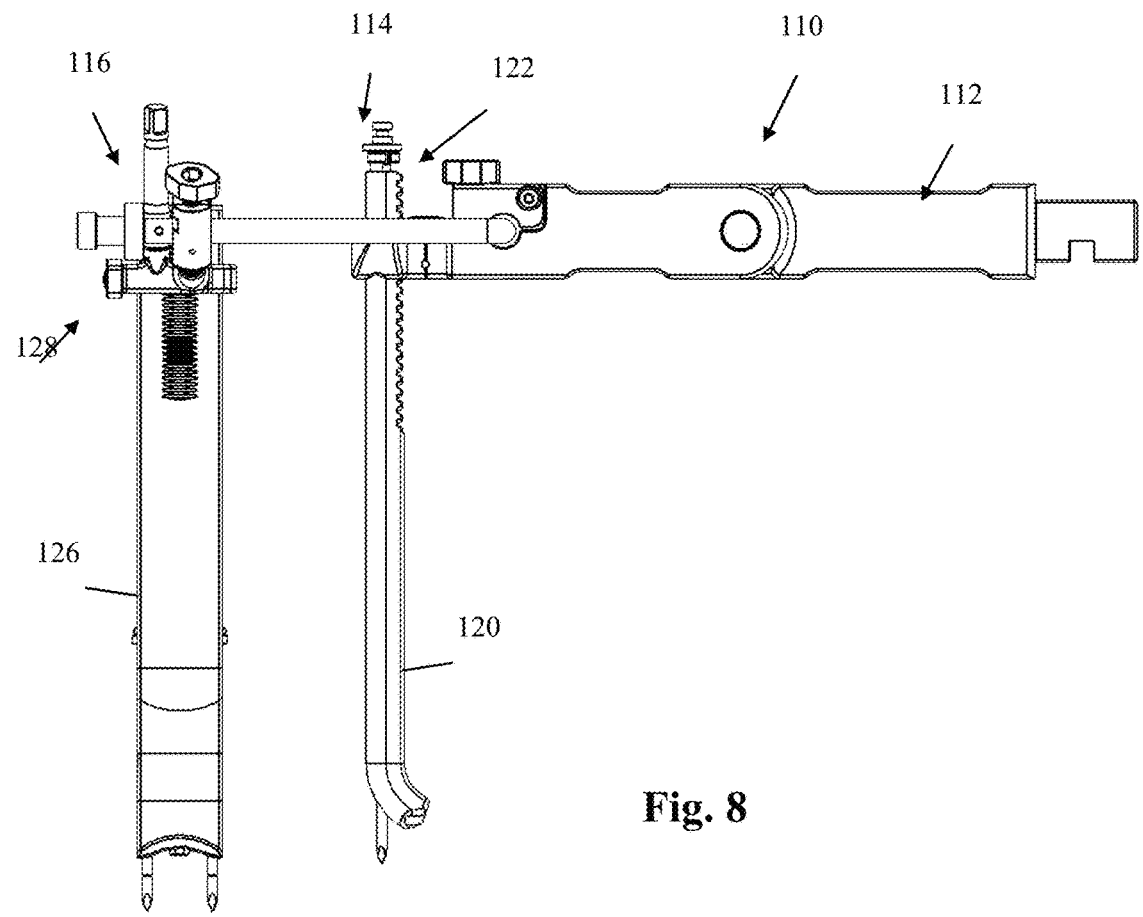
FIG. 8 is a side plan view of the surgical retractor system of FIG. 5.
Figure 9:
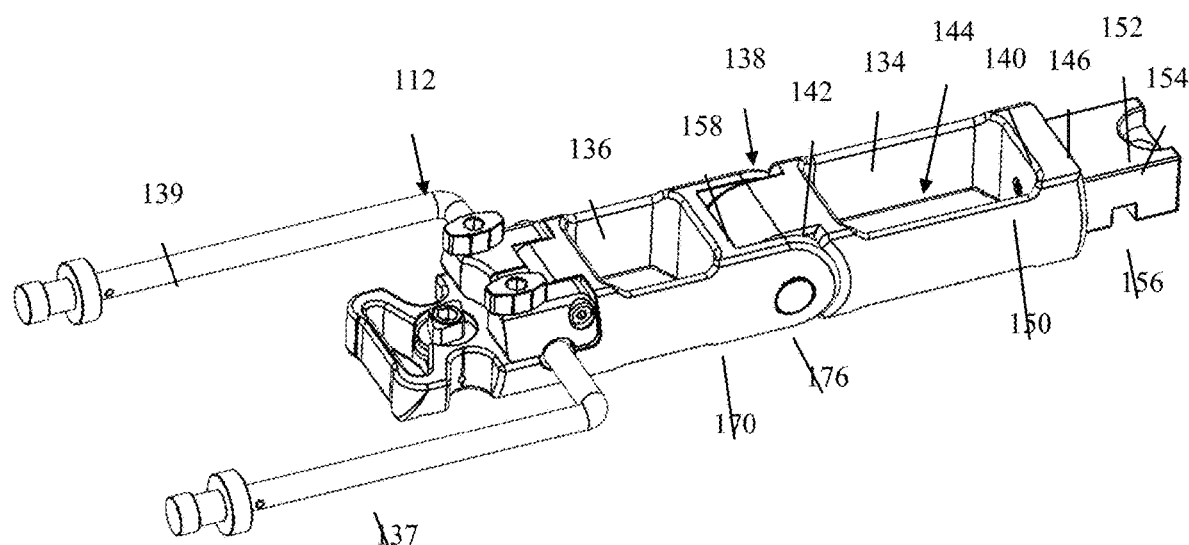
FIG. 9 is an elevated perspective view of an example of a retractor body forming part of the surgical retractor system of FIG. 5.
Figure 10:
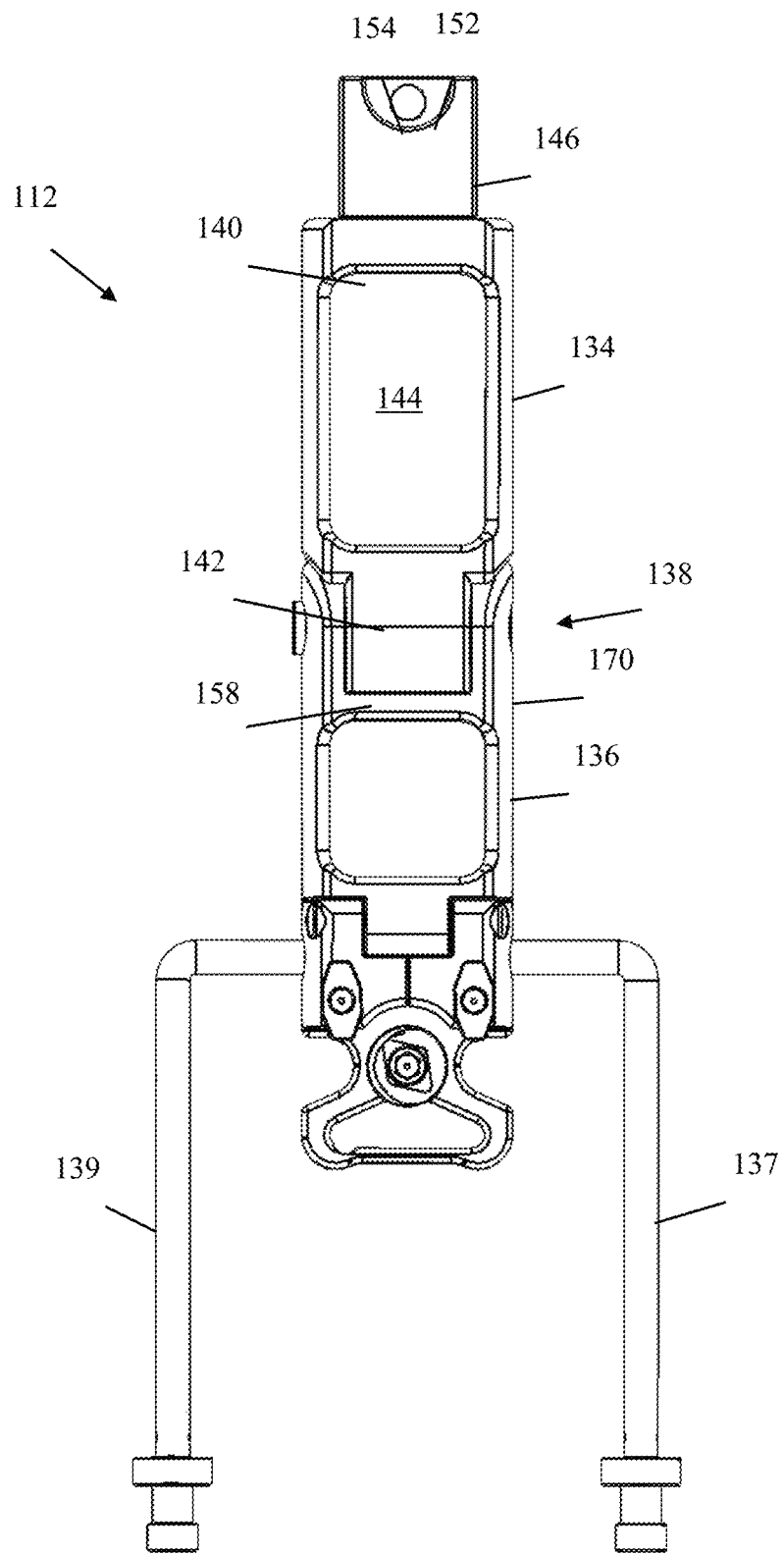
FIG. 10 is a top plan view of the retractor body of FIG. 9.

With reference to FIGS. 1-4, a retractor system 10 of the present invention includes a handle 12, a first adjustable blade assembly 14, a second adjustable blade assembly 16, and a third adjustable blade assembly 18. First blade assembly 14 includes a first blade 20 coupled to a first articulation assembly 22 that is, in turn, coupled to an arm 24 extending from the handle 12. Second blade assembly 16 includes a second blade 26 coupled to a second articulation assembly 28 that is, in turn, coupled to an arm 30 extending from the handle 14. Third blade assembly 18 includes a third blade 32 coupled to a third articulation assembly 34 that is, in turn, coupled to a pair of parallel arms 35 extending from the handle 12. As shown in FIG. 3, handle 12 includes a generally horizontal section 12H and generally vertical section 12V, each of which may be dimensioned to be manually grasped by a surgeon or physician's assistant (PA) intra-operatively and may also include features to secure the handle 12 in a stationary manner relative to the patient and/or the operating table.

The first articulation assembly 22 includes a first arm 36, a second arm 38, and a lock bolt 39. The first arm 36 includes an articulation housing 40 at a first end and an elbow joint element 42 at a second end. The articulation housing 40 is dimensioned to receive a balled element 43 extending from the arm 24 of the handle 12. The second arm 38 includes an articulation housing 44 at a first end and an elbow joint 46 at a second end. The articulation housing 44 is dimensioned to receive a balled element 45 extending from a first blade holder assembly 47 coupled to the first blade 20. The lock bolt 39 extends through axially aligned apertures in the elbow joints 42, 46 and includes an enlarged region 39a dimensioned to be manually rotated by a user to lock or unlock the articulation assembly 22. More specifically, the manual rotation of the lock bolt 39 will serve to lock or unlock the elbow joints 42, 46, the articulating joint formed between the articulation housing 40 and the balled element 43 forming part of the arm 24 of the handle 12, and the articulation joint formed between the articulation housing 44 and the balled element 45 extending from the first blade holder assembly 47. Each articulation joint so formed is capable of articulating in multiple planes and also rotationally, which collectively provides a high degree of flexibility in positioning the first blade 20 relative to the handle 12, second blade 26 and third blade 32 to create a customized operative corridor.

The second articulation assembly 28 includes a first arm 56, a second arm 58, and a lock bolt 59. The first arm 56 includes an articulation housing 60 at a first end and an elbow joint element 62 at a second end. The articulation housing 60 is dimensioned to receive a balled element 63 extending from the arm 30 of the handle 12. The second arm 58 includes an articulation housing 64 at a first end and an elbow joint 66 at a second end. The articulation housing 64 is dimensioned to receive a balled element 65 extending from a second blade holder assembly 67 coupled to the second blade 26. The lock bolt 59 extends through axially aligned apertures in the elbow joints 62, 66 and includes an enlarged region dimensioned to be manually rotated by a user to lock or unlock the articulation assembly 28. More specifically, the manual rotation of the lock bolt 59 will serve to lock or unlock the elbow joints 62, 66, the articulating joint formed between the articulation housing 60 and the balled element 63 forming part of the arm 30 of the handle 12, and the articulation joint formed between the articulation housing 64 and the balled element 65 extending from the second blade holder assembly 67. Each articulation joint so formed is capable of articulating in multiple planes and also rotationally, which collectively provides a high degree of flexibility in positioning the second blade 26 relative to the handle 12, first blade 20 and third blade 32 to create a customized operative corridor.

The third articulation assembly 34 includes a lock bolt that extends perpendicularly through the pair of parallel arms 35 that extend longitudinally away from the handle 12 along the longitudinal axis of the handle 12, as well as through a bore formed through part of a third blade holder assembly 73 coupled to the third blade 32. The lock bolt 37 of the third articulation assembly 34 may be operated with a wrench, driver, or other instrument capable of rotating the lock bolt 37 clockwise or counterclockwise to tighten or loosen, respectively, the articulation joint so formed. Based on the perpendicular positioning of the lock bolt 37, the degree of articulation of the third blade 32 is limited to the plane of the longitudinal axis of the handle 12, that is, the third blade 32 may be selectively tilted relative to the handle 12 but not rotated or positioned outside the plane of the longitudinal axis of the handle 12. The uni-planar articulation joint of the third articulation assembly 34 provides a lower yet important degree of flexibility in positioning the third blade 32 relative to the handle 12, first blade 20 and second blade 26 to collectively create a customized operative corridor.

The first, second and third blades 20, 26, 32 may be constructed having any number of suitable features and dimensions. In one embodiment, the first blade 20 and second blade 26 are generally identical in construction, each dimensioned such that, in use, a proximal end (20P and 26P in FIG. 4) will extend above the skin of the patient and a distal end (20D and 26D in FIG. 4) will extend to a location proximate the surgical target site. The third blade 32 is of similar construction to the first blade 20 and second blade 26, with the exception that the third blade 32 includes longitudinal apertures 69 for receiving K-wires or other fixation elements to dock or otherwise temporarily register the distal end of the third blade 32 relative to the surgical target site (e.g. by extending the fixation element into the adjacent vertebral bodies and/or the disc space). The third blade 32 also differs from the first and second blades 20, 26 in that the distal end (32D in FIG. 4) of the third blade 32 includes a notch 71 extending along the perimeter as best viewed in FIG. 4. The blades 20, 26, 32 may be constructed from any number of suitable materials, including but not limited to metal, carbon fiber, plastic or any combination.

The length of the blades 20, 26, 32 that extends between a skin incision and the surgical target site may be selectively adjusted through the use of the respective blade holder assemblies 47, 67, 73. First blade holder assembly 47 includes a collar 75 having an aperture dimensioned to slidably receive the first blade 20 therethrough, as well as a screw 76 for selectively locking or unlocking the first blade 20 relative to the collar 75. Second blade holder assembly 67 includes a collar 85 having an aperture dimensioned to slidably receive the second blade 26 therethrough, as well as a screw 86 for selectively locking or unlocking the second blade 26 relative to the collar 85. Third blade holder assembly 73 includes a collar 95 having an aperture dimensioned to slidably receive the third blade 32 therethrough, as well as a screw 96 for selectively locking or unlocking the third blade 32 relative to the collar 95. In this manner, the length of each blade 20, 26, 32 extending between skin incision and surgical target site may be independently adjusted such that the distal ends 20D, 26D, 32D may be positioned with different lengths to accommodate an optimal location relative to the surgical target site. This may be especially advantageous during surgeries wherein the surgical approach is at an angle relative to the surgical target site, such as (by way of example only) during a retroperitoneal surgical approach to the L5-S1 disc space, which methodology is explained in greater detail U.S. Pat. No. 9,451,940, the complete disclosure of which is incorporated by reference into this disclosure as if set forth fully herein.

FIGS. 5-49 illustrate a surgical retractor system 110 according to another embodiment of the disclosure. With initial reference to FIGS. 5-8, the surgical retractor system 110 of the present example includes a retractor body 112, a first blade assembly 114, a second blade assembly 116, and a third blade assembly 118. As will be described in further detail below, the first blade assembly 114 includes a first retractor blade 120 and a first blade holder assembly 122 including a blade holder 124 integrally formed with (or otherwise attached directly to) the distal body portion 136 of the retractor body 112 (see, e.g. FIG. 17). The second blade assembly 116 includes a second retractor blade 126 and a second blade holder assembly 128 movably coupled to a first arm 137 of the retractor body 112. More specifically, the second blade holder assembly 128 may be caused to translate longitudinally along and/or rotate about the first arm 137 which, when also including a pivoting motion within the blade holder assembly 128 as well as vertical adjustment capability of the second retractor blade 126, allows the user to position the second retractor blade 126 in any suitable manner to create a customizable operative corridor. The third blade assembly 118 includes a third retractor blade 130 movably coupled to a second arm 139 of the retractor body 112. More specifically, the third blade holder assembly 132 may be caused to translate longitudinally along and/or rotate about the second arm 139 which, when also including a pivoting motion within the blade holder assembly 132 as well as vertical adjustment capability of the third retractor blade 130, allows the surgeon to position the third retractor blade 130 in any suitable manner to create a customizable operative corridor. By way of example, the retractor body 112 has a longitudinal axis 1 extending therethrough that effectively divides the retractor body into two sides (e.g. a first side and a second side).

The blades 120, 126, 130 may be constructed from any number of suitable materials, including but not limited to metal, carbon fiber, plastic or any combination. The length of the blades 120, 126, 130 that extends between a skin incision and the surgical target site may be selectively and independently adjusted through the use of the respective blade holder assemblies 122, 128, 132. As such, the distal ends of each of the blades may be positioned with different lengths to accommodate an optimal location relative to the surgical target site. This may be especially advantageous during surgeries wherein the surgical approach is at an angle relative to the surgical target site, such as (by way of example only) during a retroperitoneal surgical approach to the L5-S1 disc space, which methodology is explained in greater detail U.S. Pat. No. 9,451,940, the complete disclosure of which is incorporated by reference into this disclosure as if set forth fully herein.

FIGS. 9-16 illustrate an example of the retractor body 112 forming part of the surgical retractor system 110 according to one aspect of the disclosure. By way of example, the retractor body 112 includes a proximal body portion 134, a distal body portion 136, and first and second retractor arms 137, 139 coupled with and extending from the distal body portion 136. In the example shown and described herein, the proximal body portion 134 are separate elements joined by a hinge joint 138, however other formations are possible.

By way of example, the proximal body portion 134 has a proximal end 140, a distal end 142, and an enlarged cutout section 144 that primarily functions to reduce the amount of material used (and therefore the weight of the retractor). By way of example, the proximal body portion 134 may also be considered as a "handle" element to allow for manual manipulation by a user. In addition, the retractor body 112 may further include a proximal connector 146 coupled to and extending proximally from the proximal end 140. The proximal connector 146 of the present example is a generally rectangular member including a threaded post 148 extending distally therefrom and configured to be threadedly received within a proximal threaded aperture 150 formed within the proximal end 140 of the proximal body portion 134 (however other engagement mechanisms are possible, including but not limited to snap-fit, welding, and integral formation). The proximal connector 146 further includes an upper-facing cutaway 152 positioned at the proximal end which itself includes a recess 154 formed therein, and a lower-facing recess 156 extending laterally and/or longitudinally across the inferior surface of the proximal connector 146. By way of example, the upper-facing cutaway 152, recess 154, and/or lower-facing recess 156 may facilitate engagement of the retractor body 112 with additional instrumentation and/or structure (e.g. articulating arm) to secure the retractor body 112 in a stationary manner relative to the patient and/or the operating table.

The distal end 142 includes a flange 158 extending distally from the distal end 142, the flange 158 forming part of the hinge joint 138 connecting the proximal body portion 134 to the distal body portion 136. The flange 158 includes a transverse through-hole 160 extending laterally through the flange 158 and dimensioned to receive the shaft 178 of the hinge pin 176 therein. The distal end 142 further includes a pair of cutout regions 162 flanking the flange 158 (one cutout region 162 on either side of the flange 158) that are each sized and dimensioned to receive one of the proximal extensions 170 of the distal body portion 136, while allowing relative movement between the proximal body portion 134 and distal body portion 136 (e.g. partial rotation about the axis of the hinge pin 176).

The distal body portion 136 (shown by way of example in FIGS. 12-14) has a proximal end 164, a distal portion 166 including a distal end 167, and an enlarged cutout section 168 positioned between the proximal end 164 and distal portion 166 that primarily functions to reduce the amount of material used (and therefore the weight of the retractor). As will be described in detail below, the proximal end 164 includes structure that forms part of the hinge joint 138, while the distal portion 166 includes structure enabling the coupling of the retractor arms 137, 139 to the retractor body 112, as well as structure related to the first blade holder assembly 122. The proximal end 164 includes a pair of proximal extensions 170 extending in a proximal direction from the proximal end 164 and spaced apart laterally by a distance that corresponds generally to the width of the flange 158, thereby creating a void 172 between the proximal extensions 170 that is sized and configured to receive the flange 158 therein. Each proximal extension 170 includes a lateral aperture 174 sized and configured to interact with the hinge pin 176 and positioned to be coaxial with the transverse through-hole 160 of the flange 158 when the flange 158 is positioned within the void 172.

The hinge joint 138 comprises the flange 158 of the proximal body portion 134, the proximal extensions 170 of the distal body portion 136, and a hinge pin 176 that secures the proximal body portion 134 to the distal body portion 136 and provides a cylindrical surface about which both the proximal body portion 134 (via flange 158) and distal body portion 136 (via proximal extensions 170) may rotate. The hinge pin 176 comprises a cylindrical shaft 178 having cylindrical head 180 at one end that has a diameter greater than the diameter of the shaft 178 and a threaded aperture (not shown) at the other end (see FIG. 11). The threaded aperture of the shaft 178 is configured to mate with a hinge screw 182, and particularly a threaded post 184 thereof. The hinge screw 182 further comprises a head portion 186 including a driver recess (not shown) for engagement with a driver instrument. Each lateral aperture 174 includes a circumferential ledge 188 positioned therein. The circumferential ledges 188 enable the passage of the cylindrical shaft 178 therethrough but not the cylindrical head 180 of the hinge pin 176 or the head portion 186 of the hinge screw 182. The hinge screw 182 may be actuated by a driver such that rotation in a clockwise direction draws the cylindrical head 180 of the hinge pin 176 and head portion 186 of the hinge screw 182 toward one another, which due to their respective interaction with the circumferential ledges 188 creates a compressive force acting on the proximal extensions 170 and flange 158, effectively "tightening" the construct to secure the proximal and distal body portions 134, 136 in a desired angular relationship. The angle may be re-adjusted after rotating the hinge screw 182 in a counterclockwise direction to "loosen" the construct by relieving the compressive force on the proximal extensions 170 and flange 158.

The distal portion 166 includes a generally planar superior surface 190, a generally planar inferior surface 192, and a protrusion 194 extending vertically from the superior surface 190. The vertical protrusion 194 is positioned adjacent to the enlarged cutout section 168 along the longitudinal axis 1, and has a pair of threaded apertures 196 formed therein in a transverse direction relative to the longitudinal axis. The threaded apertures 196 are each configured to receive the threaded post 260 of an arm cap hinge screw 240 (see e.g. FIG. 15). The vertical protrusion may also include a transverse through-hole 198 formed therein to reduce the amount of material used to manufacture the retractor body 112 (thereby reducing the weight of the device). The superior surface 190 includes first and second concave recesses 200, 202 positioned on either side of the distal body portion 136 adjacent to the vertical protrusion 194. The concave recesses 200, 202 are sized and configured to receive at least a portion of the generally spherical proximal ends 226 of the first and second retractor arms 137, 139, respectively. The superior surface 190 further includes a pair of vertically-oriented threaded apertures 204 positioned adjacent the concave recesses 200, 202, each configured to receive the threaded post 266 of an arm cap lock screw 242 (see e.g. FIG. 15).

The distal end 167 of the distal portion 166 comprises the blade holder 124 which includes a blade aperture 206 extending vertically through the blade holder 124, the blade aperture 206 being sized and configured to receive the first retractor blade 120 therein. The superior surface 190 further includes a generally cylindrical recess 208 formed therein and positioned on the longitudinal axis immediately adjacent the blade aperture 206 such that the blade aperture 206 and recess 208 are adjoining via a pass-through 210. The generally cylindrical recess 208 is sized and configured to receive at least a portion of the blade adjustment member 294 (see FIG. 17). The cylindrical recess 208 further includes a bottom surface 212 having a circular aperture 214 extending therethrough, the diameter of the aperture 212 being less than the diameter of the cylindrical recess 208. The inferior surface 192 has a shaped recess 216 formed therein about the inferior egress of the circular aperture 214. The inferior recess 216 has a peripheral shape corresponding to the peripheral shape of the bottom plate 298, and includes a threaded aperture 218 formed therein to receive a threaded post portion of a bottom plate lock screw (not shown). A pair of lateral cutout sections 220 are provided laterally adjacent to the cylindrical recess 208, for example to provide increased visibility of the operative corridor for the surgeon.

Figure 11:
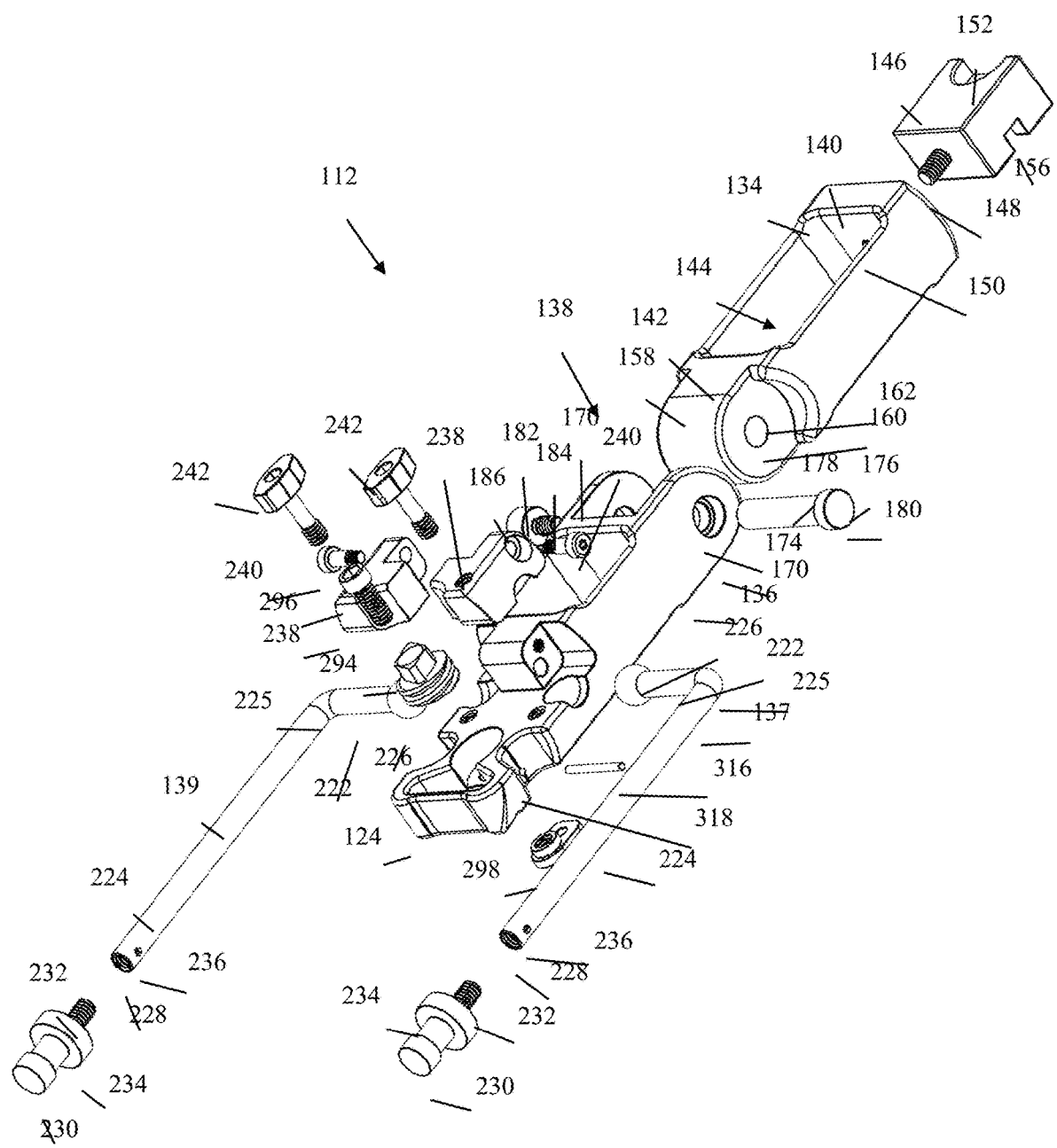
FIG. 11 is an exploded perspective view of the retractor body of FIG. 9.
Figure 12:
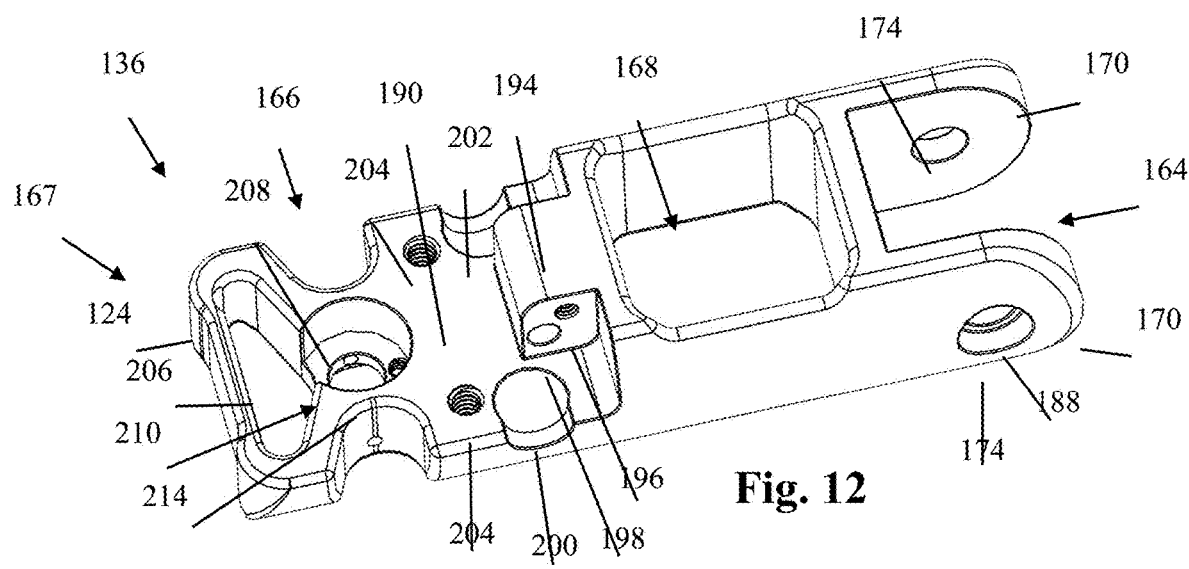
FIG. 12 is an elevated perspective view of a base member forming part of the retractor body of FIG. 9.
Figure 13:
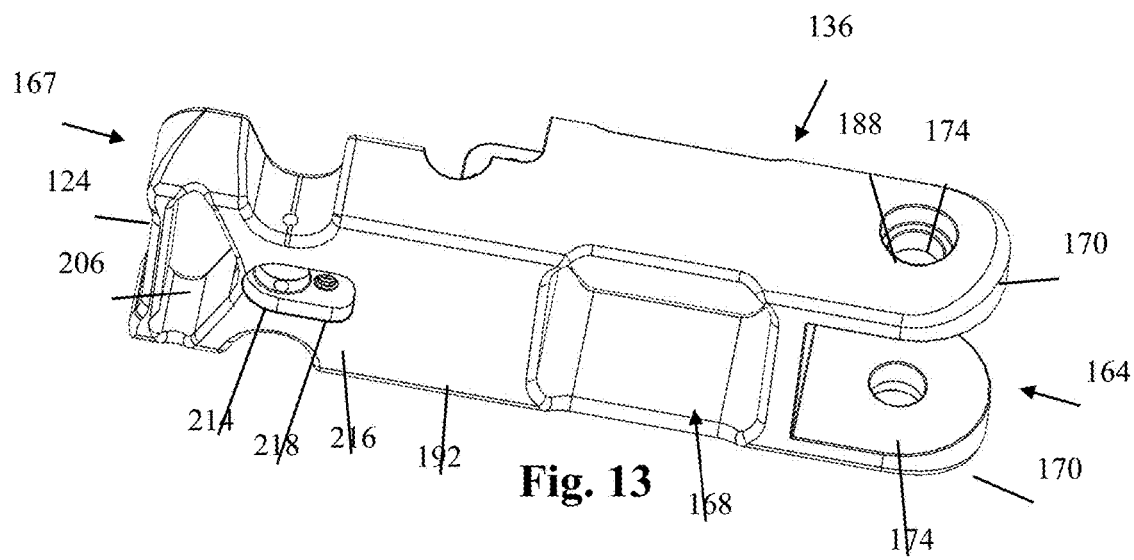
FIG. 13 is a bottom perspective view of the base member of FIG. 12.
Figure 14:
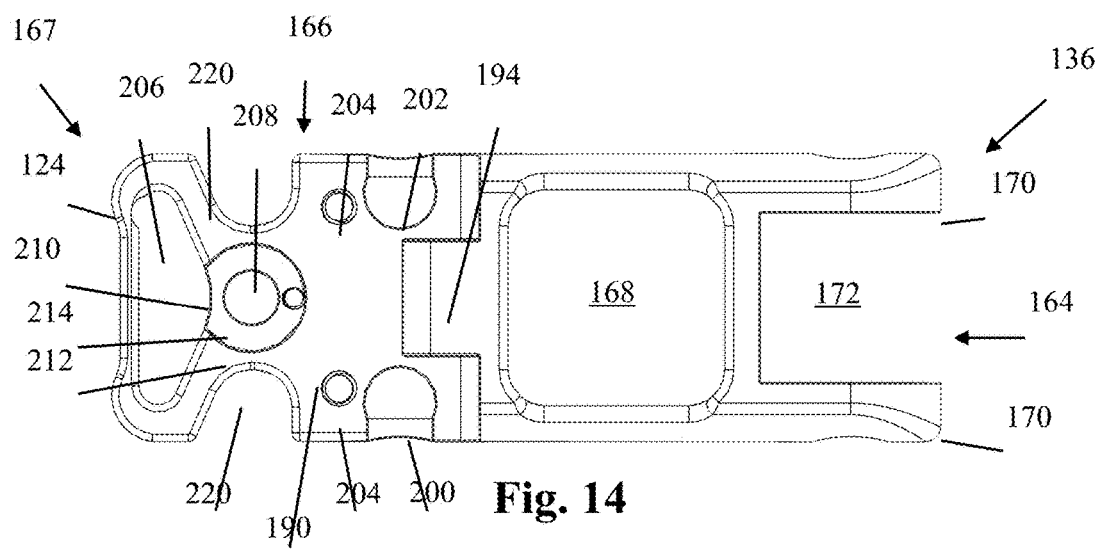
FIG. 14 is a top plan view of the base member of FIG. 12.
Figure 15:
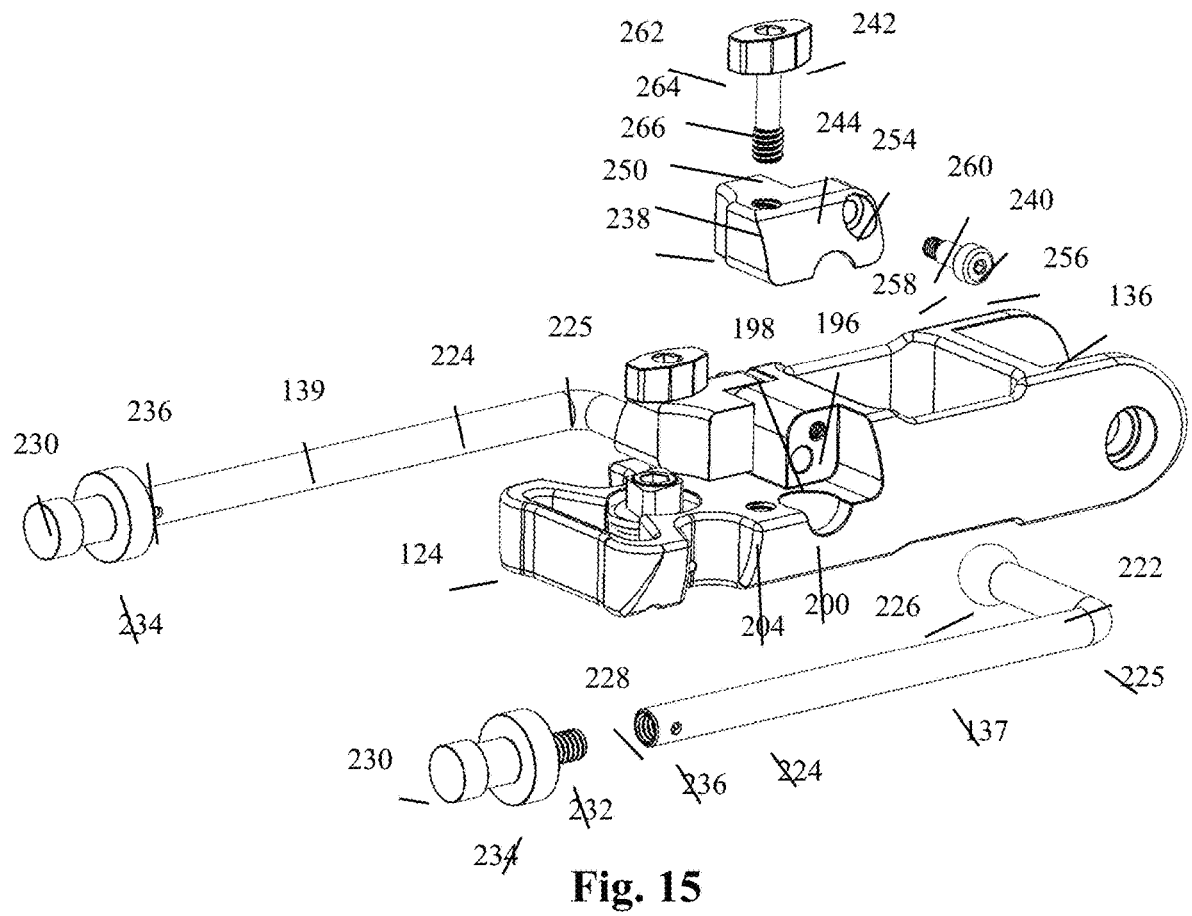
FIG. 15 is a partially exploded elevated perspective view of the retractor body of FIG. 9.
Figure 16:
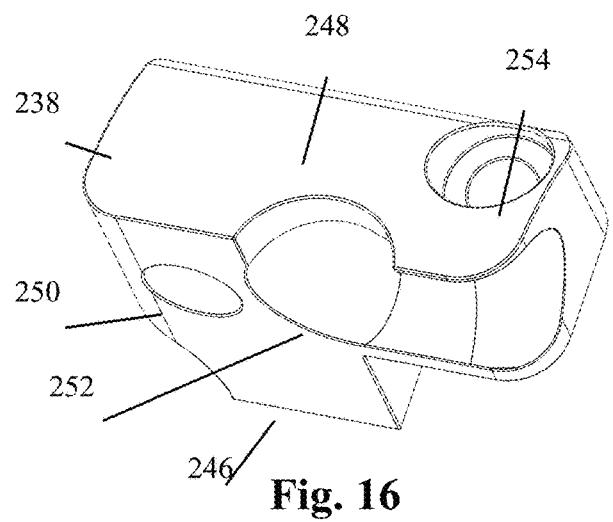
FIG. 16 is a bottom perspective view of a cap member forming part of the retractor body of FIG. 9.
Figure 17:
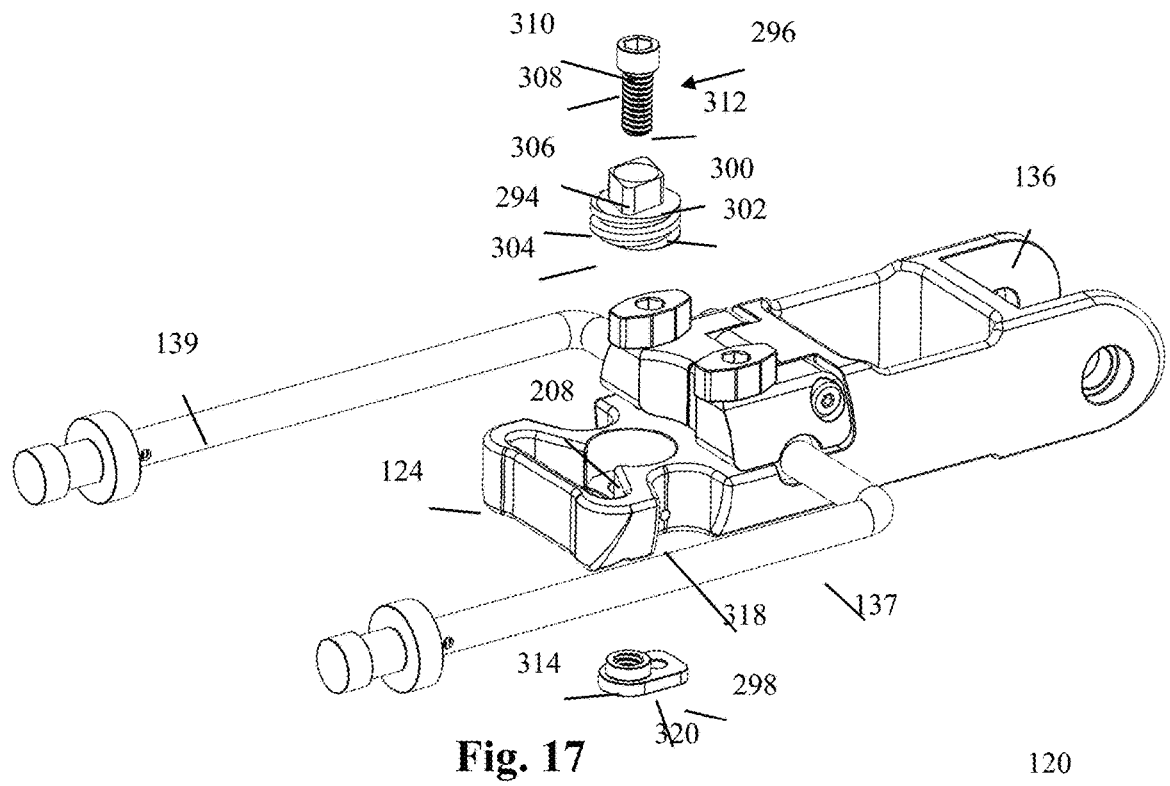
FIG. 17 is a partially exploded elevated perspective view of the retractor body of FIG. 9.
Figure 18:
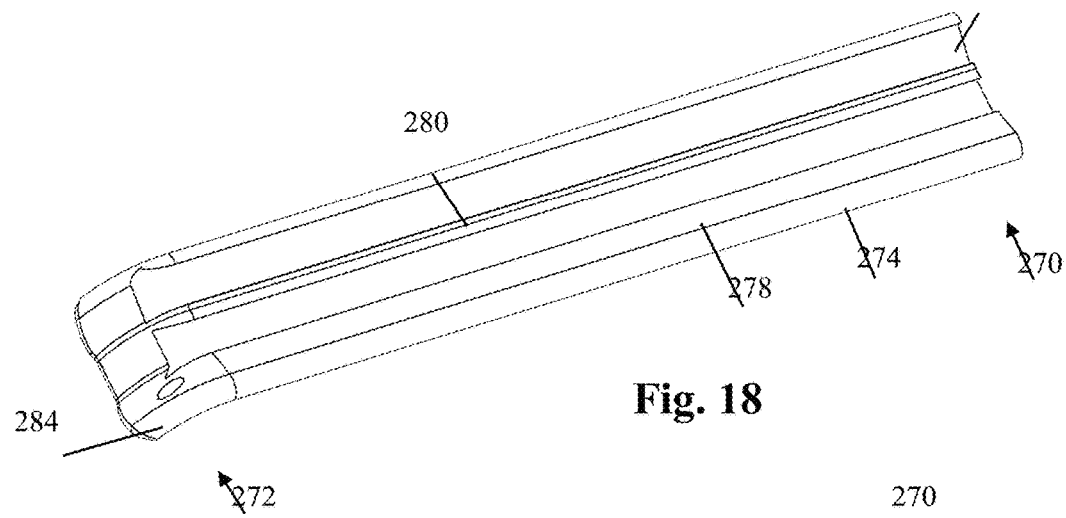
FIG. 18 is an elevated perspective view of a first retractor blade forming part of the surgical retractor system of FIG. 5.
Figure 19:
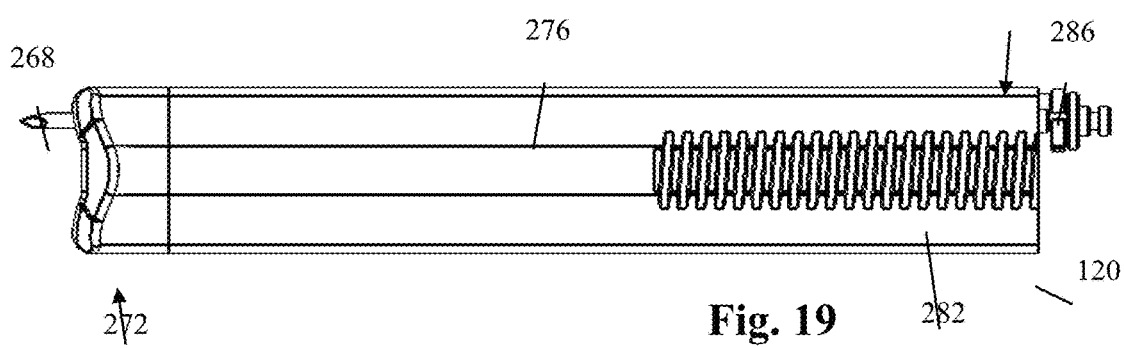
FIG. 19 is a front plan view of one example of a first blade assembly forming part of the surgical retractor system of FIG. 5.
Figure 20:
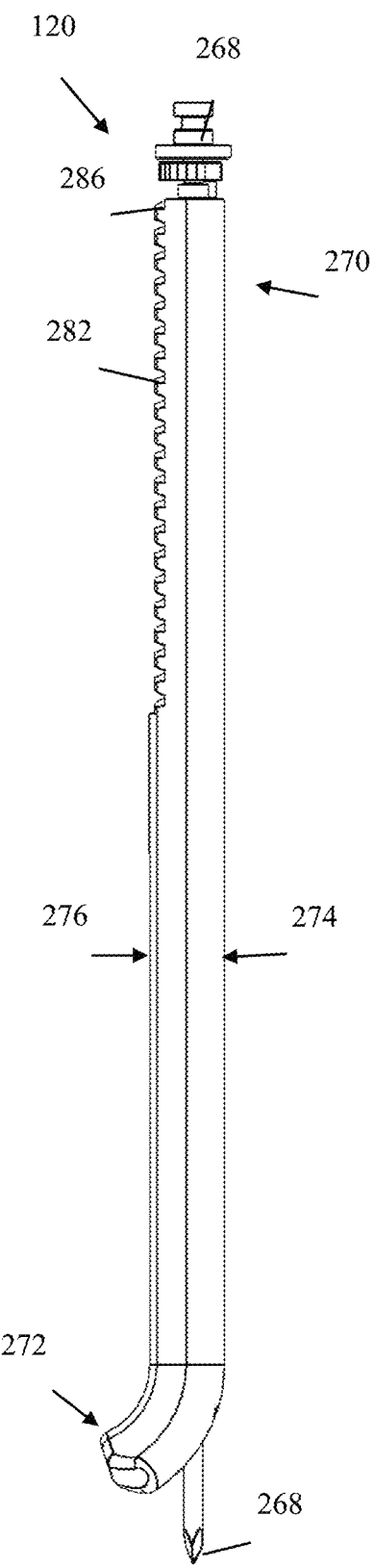
FIG. 20 is a side plan view of the first retractor blade assembly of FIG. 19.
Figure 21:
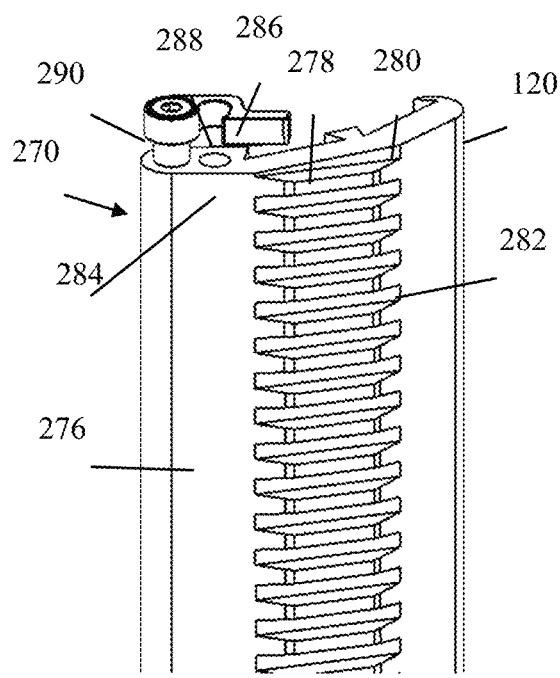
FIG. 21 is a rear elevated perspective view of an upper portion of the first retractor blade assembly of FIG. 19.
Figure 22:
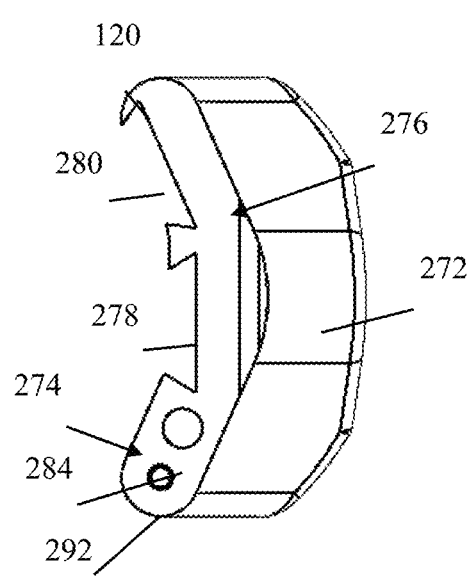
FIG. 22 is a top plan view of the first retractor blade of FIG. 18.
Figure 27:
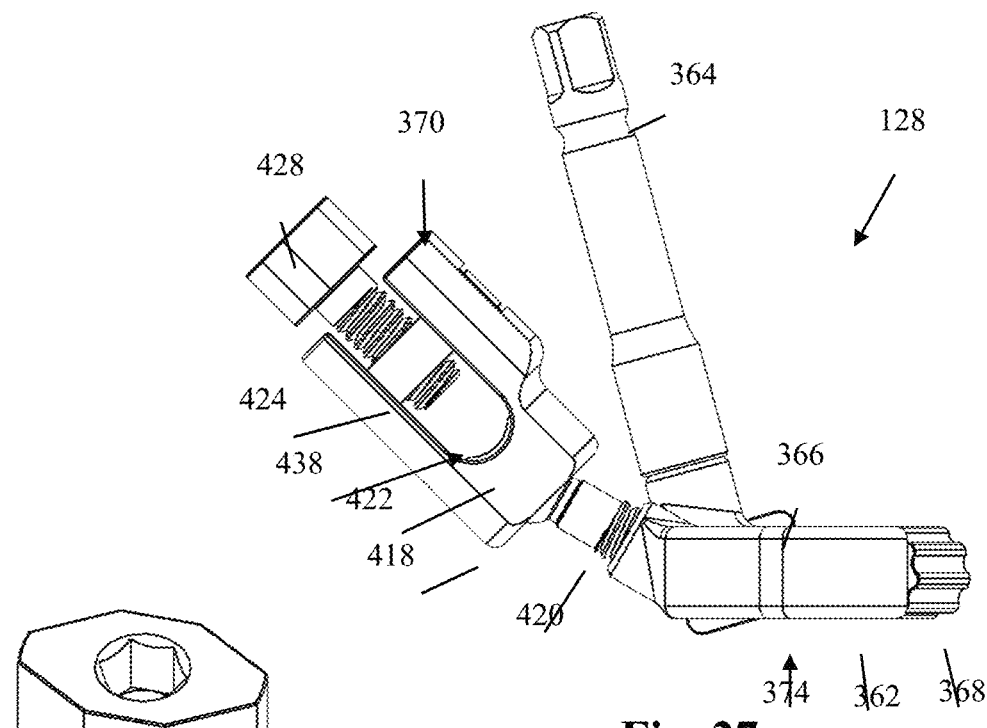
FIG. 27 is a side plan view of the blade holder assembly of FIG. 24.
Figure 28:
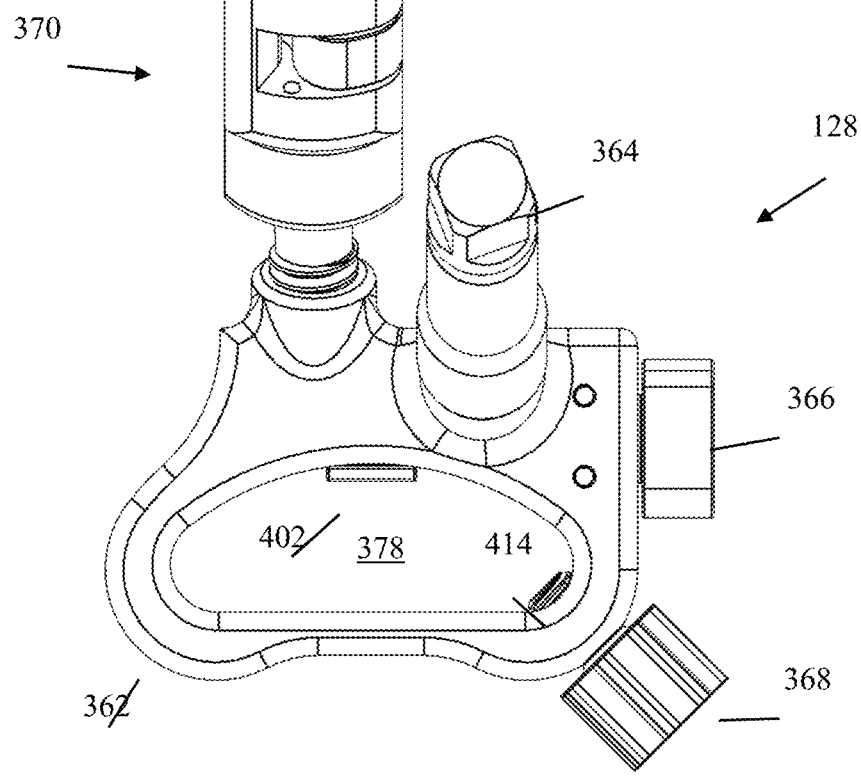
FIG. 28 is a top plan view of the blade holder assembly of FIG. 24.
Figure 29:
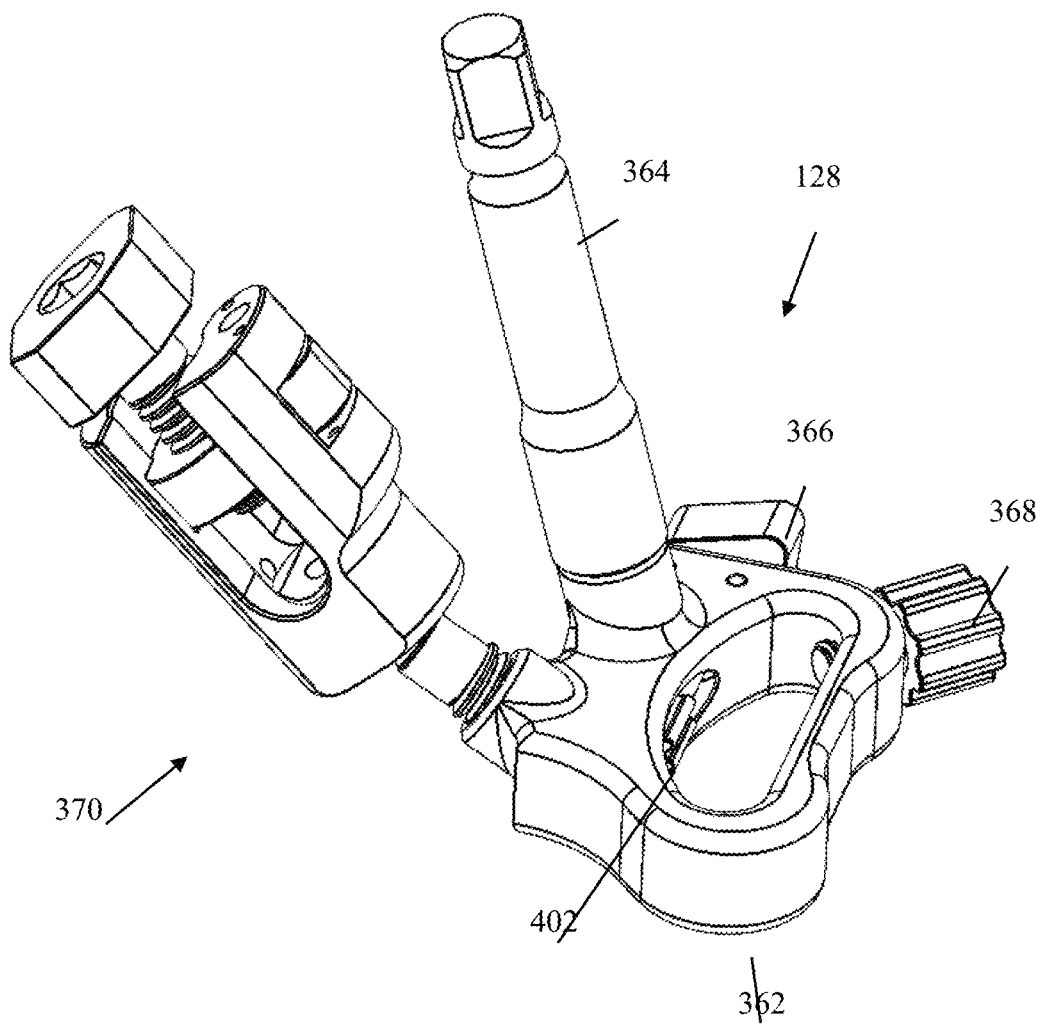
FIG. 29 is a front elevated perspective view of the blade holder assembly of FIG. 24.

FIGS. 11 and 15-16 illustrate the components related to the retractor arms 137, 139 in more detail. Specifically, FIG. 11 illustrates all components in exploded form. FIG. 15 illustrates the components related to one retractor arm (e.g. second retractor arm 139) in exploded form. FIG. 16 illustrates an arm cap 238 in isolation. It should be understood that the first and second retractor arms 137, 139 and their corresponding assembly components are either identical to or mirror images of each other. Therefore, for the purpose of illustration and in the interest of brevity, like elements and assembly components have been assigned the same reference number. As previously described, the first and second retractor arms 137, 139 extend from the distal body portion 136 of the retractor body 112. By way of example, each retractor arm 137, 139 is a generally "L"-shaped cylindrical member having a lateral portion 222 and a longitudinal portion 224 joined by a generally perpendicular elbow junction 225. In the example shown, the lateral portion 222 comprises the proximal short segment of the "L" shape and terminates with a generally spherical proximal end 226. The longitudinal portion 224 comprises the distal long segment of the "L" shape and terminates with an axially-formed threaded aperture 228. The first retractor arm 137 is positioned such that the generally spherical proximal end 226 is received within the first concave recess 200, and the second retractor arm 139 is positioned such that the generally spherical proximal end 226 is received within the second concave recess 202. In both cases, the lateral portion 222 extends generally laterally from one side of the distal body portion 136 (e.g. transverse to the longitudinal axis 1 and in opposite directions from each other), and the longitudinal portion 224 extends distally in a direction generally parallel to the longitudinal axis 1. An arm stop 230 is provided having a threaded post 232 configured to mate with the threaded aperture 228 and a head portion 234 having a diameter larger than the diameter of the longitudinal portion 224 to provide translation stops for the second and third blade holder assemblies 128, 132. A lock pin (not shown) may be provided that extends transversely through lock pin apertures 236 in the retractor arms 137, 139 and an axially aligned aperture (not shown) in the threaded post 232 to lock the arm stop 230 to the corresponding retractor arms 137, 139.

Each retractor arm 137, 139 is secured within the concave apertures 200, 202, respectively, by way of an arm cap 238.

The arm caps 238 are hingedly secured to the distal body portion 136 by way of arm cap hinge screws 240. As will be explained, the arm caps 238 allow for independent adjustability of each retractor arm 137, 139 and are capable of being locked in place (and also unlocked for readjustment) by way of the arm cap lock screws 242. By way of example, each arm cap 238 has a superior surface 244, inferior surface 246, and an outward facing (e.g. away from the longitudinal axis 1) lateral surface 248. The superior surface 244 includes a vertically-oriented, nonthreaded through-hole 250 (which extends to the inferior surface 246) sized and configured to receive the post 264 of an arm cap lock screw 242 therethrough. The inferior surface 246 includes a concave recess 252 sized and configured to receive at least a portion of the generally spherical proximal end 226 of one of the retractor arms 137, 139 therein. The lateral surface 248 includes a laterally-oriented through-hole 254 configured to receive the post 258 of an arm cap hinge screw 240 therethrough.

When the arm caps 238 are placed in position on the distal body portion 136, the laterally-oriented through-holes 254 are axially aligned with the threaded apertures 196 on either side of the vertical protrusion 194. Each arm cap hinge screw 240 includes a head 256 and a shaft 258 including a distal threaded portion 260 extending from the head 256. The shaft 258 is inserted through the lateral through-hole 254 such that the distal threaded portion 260 is threadedly engaged with the threaded apertures 196. When the arm cap hinge screw 240 is fully inserted and the arm cap lock screw 242 is in an "unlocked" position, the arm cap 238 may pivot slightly about the shaft 258 of the arm cap hinge screw 240 in response to any adjustment of the retractor arms 137, 139. When the arm cap lock screw 242 is in a "locked" position, the arm cap 238 does not move.

Similarly, when the arm caps 238 are placed in position on the distal body portion 136, the vertically-oriented through-holes 250 are axially aligned with the threaded apertures 204 on the superior surface 190 of the distal body portion 136. Each arm cap lock screw 242 includes a head 262 and a shaft 264 including a distal threaded portion 266 extending from the head 262. The head 262 comprises an enlarged member sized and configured to be manually manipulated by a user with or without the use of additional instrumentation. The shaft 264 is inserted through the vertical through-hole 250 such that the distal threaded portion 266 is threadedly engaged with the threaded apertures 204. When the arm cap lock screw 242 is nearly fully inserted but not tightened (e.g. in an "unlocked" position), the arm cap 238 may pivot slightly about the shaft 258 of the arm cap hinge screw 240 in response to any adjustment of the retractor arms 137, 139. The adjustment of the retractor arms 137, 139 is enabled by the interaction of the generally spherical proximal ends 226 and the concave recesses 200, 202 of the distal body portion 136 and the concave recesses 252 of the arm caps 238, and allows the lateral portion 222 of each retractor arm 137, 139 to experience a generally conical range of motion limited by the lateral openings of the aforementioned concave recesses. Rotation of the retractor arms 137, 139 is not limited. Thus, the distal ends of the retractor arms 137, 139 (including the associated retractor blade assemblies 116, 118) may be independently positionable and customizable to the specific needs of the user. When the arm cap lock screws 242 are fully tightened (e.g. in a "locked" position), the arm caps 238 exert a compressive force on the proximal ends 226 of the retractor arms 137, 139 within the concave recesses 200, 202, 252, which in turn locks the retractor arms 137, 139 in position.

With reference to FIGS. 17-23, the first blade assembly 114 includes a first retractor blade 120, a first blade holder assembly 122, and an anchor pin 268. The first retractor blade 120 may be constructed having any number of suitable features and dimensions. By way of example, the first retractor blade 120 is an elongated member having a generally rectangular peripheral shape including a length dimension and a width dimension. The first retractor blade 120 further includes a proximal end 270, a distal end 272, a first side 274, and a second side 276. During use, the proximal end 270 generally extends above the skin of a patient, the distal end 272 is positioned near the surgical target site, the first side 274 is inner-facing (e.g. facing towards the operative corridor), and the second side 276 is outer-facing (e.g. facing away from the operative corridor). The retractor blade 120 has a curvature in the width dimension such that the first side 274 has a generally concave curvature and the second side 276 has a generally convex curvature. The first side 274 includes one or more tracks for slideably receiving surgical accessories such as a shim or light source (for example). By way of example, the first side 274 includes a first track 278 extending the longitudinal length of the first blade 120 and positioned near the middle of the first side 274, and a second track 280 positioned near one lateral edge of the first blade 120 and extending the longitudinal length of the blade. The tracks 278, 280 may have any cross-sectional shape including but not limited to the dovetail shape shown by way of example in FIG. 22. The second side 276 includes a plurality of laterally oriented ridges 282 positioned at the proximal end 270. The ridges 282 are positioned at an oblique angle relative to a longitudinal axis of the first blade 120, with an angle complimentary to that of the helical flange 304 of the blade adjustment member 294.

The first retractor blade 120 further includes a longitudinal aperture 284 extending the longitudinal length of the blade 120 and positioned on the side opposite the side of the second track 280. The longitudinal aperture 284 is size and configured to receive the anchor pin 268 (e.g. K-wire, Steinman pin, etc.) therethrough. A clip 286 configured to releasably hold the anchor pin 268 in place is provided at the proximal end 270 of the first retractor blade 120. The clip includes a receptacle 288 configured to engage the engagement recess 324 of the anchor pin 268 in a snap-fit manner (for example). The clip 286 is secured to the retractor blade 120 with a lock screw 290 that is threadedly received with a lock screw aperture 292 positioned next to the longitudinal aperture 284.

The first retractor blade 120 is curved toward the second side 276 at the distal end 272. This enables the retractor blade 120 to gently engage and move anatomical structure (e.g. muscles, blood vessels, etc) away from the surgical target site as the retractor blade is adjusted.

The first blade holder assembly 122 includes a blade holder 124, blade adjustment member 294, lock screw 296, and bottom plate 298. The blade holder 124 has been described above with reference to FIGS. 12-14. By way of example, the blade adjustment member 294 comprises a head portion 300 and a generally cylindrical body portion 302 having a helical flange 304 extending around the periphery of the body portion 302. The head portion 300 comprises a shaped member sized and configured to be manually manipulated by a user with or without the use of additional instrumentation. The head portion 300 may have any shape suitable to enable a user to apply torque to the blade adjustment member 294, including but not limited to the diamond shape shown by way of example in FIG. 17.

The body portion 302 is sized and configured to be received within the cylindrical recess 208 of the retractor body 112 such that a portion of the helical flange 304 extends through the pass-through 210 into the blade aperture 206 when the blade adjustment member 294 is seated within the cylindrical recess 208 and engages the ridges 282 of the first retractor blade 120 when the first retractor blade 120 is in the blade aperture 206. The engagement of the helical flange 304 and ridges 282 is in a generally threaded manner such that when the blade adjustment member 294 is rotated in one direction (e.g. clockwise), the helical flange 304 interacts with the ridges 282 to adjust the first retractor blade 120 vertically upward, and when the blade adjustment member 294 is rotated in the opposite direction (e.g. counter-clockwise), the helical flange 304 interacts with the ridges 282 to adjust the first retractor blade 120 vertically downward. In this manner, the length of the blade 120 that extends below the skin incision may be manually adjusted by the user. The blade adjustment member 294 further comprises a nonthreaded lumen 306 extending vertically therethough, the nonthreaded lumen 306 sized and configured to allow passage of the lock screw 296.

The lock screw 296 has a head 308 including a driver recess 310 configured to engage a driver instrument and a threaded shaft 312 configured to threadedly engage the threaded aperture 314 of the bottom plate 298. The bottom plate 298 has a peripheral shape corresponding to the shape of the shaped recess 216 of the retractor body 112 (FIG. 13), and threaded interaction between threaded shaft 312 and the threaded aperture 314 results in the lock screw 296 holding the bottom plate 298 within the shaped recess 216, thereby securing the blade adjustment member 294 to the retractor body 112. Once the lock screw 296 has been fully inserted, a lock pin 316 (see FIG. 11) may be inserted through lock pin aperture 318 (and axially aligned lock pin apertures (not shown) in the lock screw 296 and threaded aperture 314) to lock the first blade holder assembly 122 to the retractor body 112. The bottom plate 298 further includes an aperture 320 formed therein adjacent the threaded aperture 314 to receive a head portion of a bottom plate lock screw (not shown).

With reference to FIG. 23, the anchor pin 268 by way of example only comprises a head 322 including an engagement recess 324, elongated shaft 326, and distal tip 328. The engagement recess 324 is sized and configured to be releasably held in the receptacle 288 of the clip 286. The elongated shaft 326 may be generally cylindrical and sized to extend through the longitudinal aperture 284 of the first retractor blade 120. The distal tip 328 has a generally pointed end that allows the anchor pine to be self-tapping. The elongated shaft 326 has a length dimension that is greater than the length dimension of the first retractor blade 120, such that the head 322 is positioned proximal of the proximal end 270 of the first blade 120 and the distal tip 328 extends distally of the distal end 272 of the first blade 120, which enables the distal tip 328 to dock or otherwise temporarily register the distal end 272 of the first blade 120 relative to the surgical target site (e.g. by extending the anchor pin 268 into the adjacent vertebral bodies and/or the disc space). For example, during a retroperitoneal surgical approach to the L5-S1 disc space, the anchor pin 268 may dock to the L5 vertebra, and remain docked for the duration of the procedure. This advantageously maintains the barrier between the surgical target site and the surrounding vasculature.

With reference to FIGS. 24-36, the second blade assembly 116 includes a second retractor blade 126 and a second blade holder assembly 128. The second retractor blade 126 may be constructed having any number of suitable features and dimensions. By way of example, the second retractor blade 126 is an elongated member having a generally rectangular peripheral shape including a length dimension and a width dimension. The second retractor blade 126 further includes a proximal end 330, a distal end 332, a first side 334, and a second side 336. During use, the proximal end 330 generally extends above the skin of a patient, the distal end 332 is positioned near the surgical target site, the first side 334 is inner-facing (e.g. facing towards the operative corridor), and the second side 336 is outer-facing (e.g. facing away from the operative corridor). The second blade 126 has a curvature in the width dimension such that the first side 334 has a generally concave curvature and the second side 336 has a generally convex curvature. By way of example, the first side 334 includes a generally smooth surface. The second side 336 includes a plurality of laterally oriented ridges 338 positioned at the proximal end 330. The ridges 338 are positioned transversely relative to a longitudinal axis of the second blade 126, and are sized and configured to interact with the gear member 402 of the blade adjustment member 366.

In the example shown and described herein, the second retractor blade 126 has three distal curves 340, 342, 344 that in effect laterally offset the distal end 332 relative to the proximal end 330 while maintaining the distal end 332 in a generally parallel orientation relative to the proximal end 330 and also forming a hook feature 346 at the distal tip 348. The first distal curve 340 is curved in the direction extending away from the first side 334. The second distal curve 342 is in the opposite direction resulting in a portion of the distal end 332 being offset but generally parallel relative to the proximal end 330. The third distal curve 344 is curved in the direction of the second side 336, resulting in the formation of a hook feature 346 at the distal tip 348. This enables the second blade 126 to initially avoid, then gently engage and move anatomical structure (e.g. muscles, blood vessels, etc.) away from the surgical target site as the second blade 126 is adjusted. The distal end 332 further includes a pair of longitudinal apertures 350 extending the longitudinal length of the offset portion of the distal end 332 and positioned on either side the first side 334. The longitudinal apertures 350 are each sized and configured to receive an anchor pin 352 therethrough. By way of example only, each anchor pin 352 includes a head 354 having a threaded post 356 extending proximally therefrom, an elongated shaft 358, and a purchase element 360 at the distal tip of the elongated shaft 358. The one or more anchor pins 352 enable the distal end 332 to dock or otherwise temporarily register the distal end 332 of the second blade 126 relative to the surgical target site (e.g. by extending into the adjacent vertebral bodies and/or the disc space). For example, during a retroperitoneal surgical approach to the L5-S1 disc space, the pins 352 may dock to the L5 vertebra, and remain docked for the duration of the procedure. This advantageously maintains the barrier between the surgical target site and the surrounding vasculature.

Figure 30:
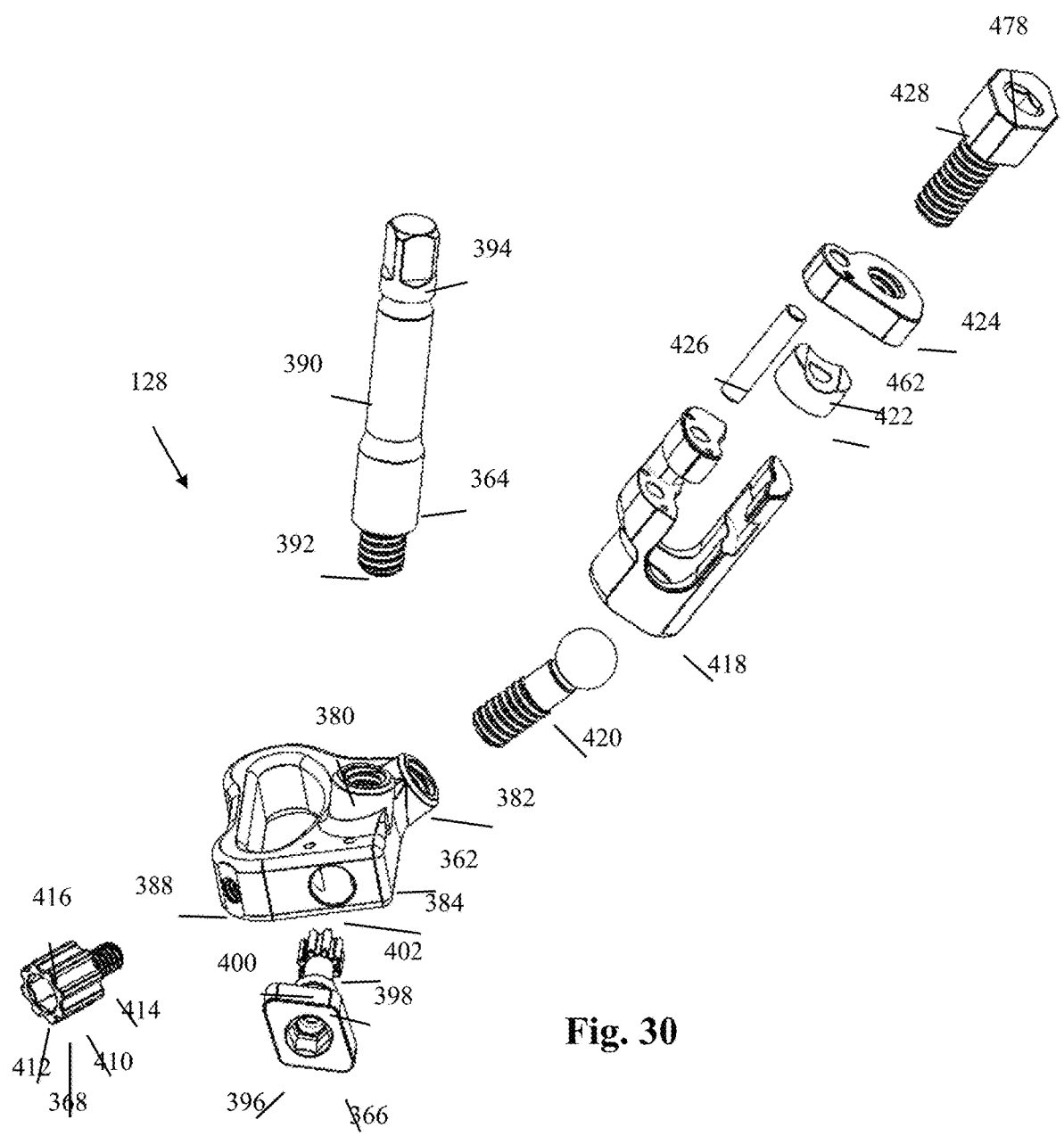
FIG. 30 is a front elevated exploded perspective view of the blade holder assembly of FIG. 24.
Figure 31:
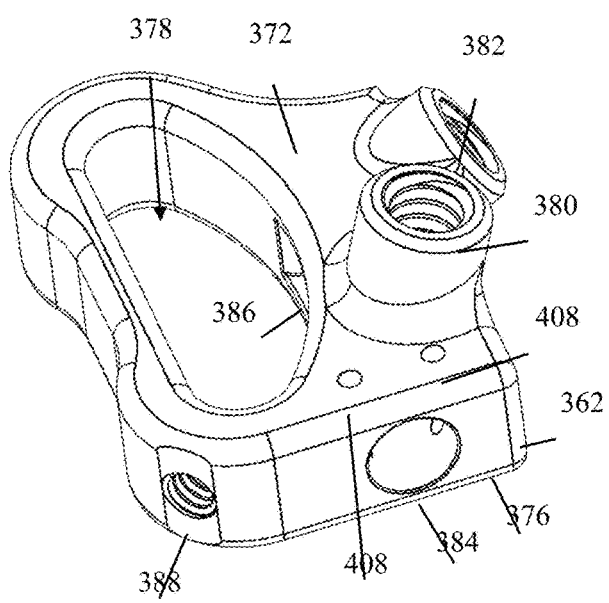
FIG. 31 is an elevated perspective view of an example of a blade holder forming part of the blade holder assembly of FIG. 24.
Figure 32:
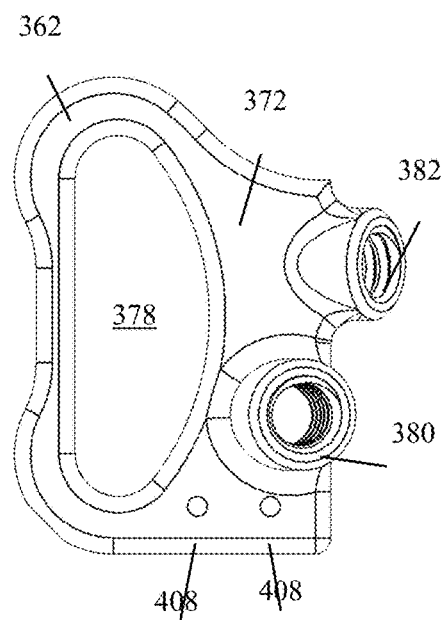
FIG. 32 is a top plan view of the blade holder of FIG. 31.
Figure 33:
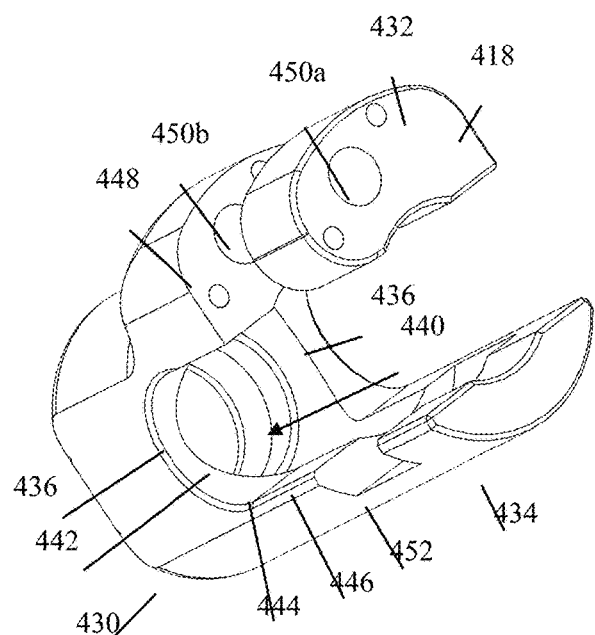
FIG. 33 is an elevated perspective view of a tulip forming part of the blade holder assembly of FIG. 24.
Figure 34:
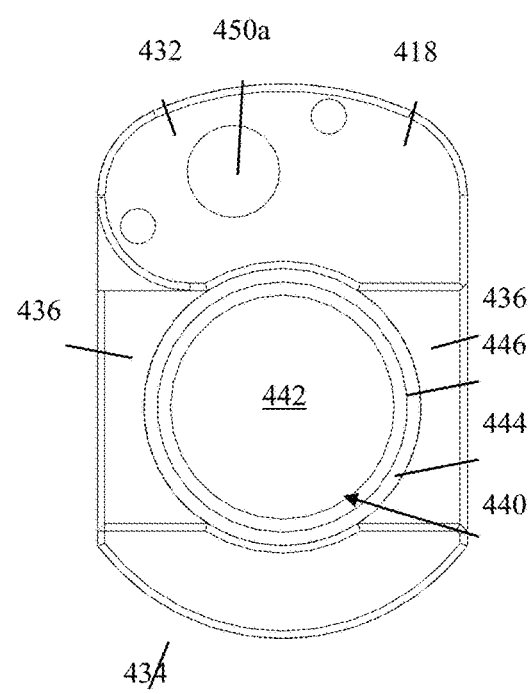
FIG. 34 is a top plan view of the tulip of FIG. 33.

The various components of the second blade holder assembly 128 are illustrated in further detail in FIGS. 27-36. By way of example only, the second blade holder assembly 128 includes a collar 362, an adjustment post 364, a blade adjustment member 366, a lock screw 368, and a tulip assembly 370. With reference to FIGS. 31-32, the collar 362 includes a superior surface 372, inferior surface 374, and a lateral surface 376 extending around the periphery of the collar 362 between the superior surface 372 and inferior surface 374. The collar 362 further includes a blade aperture 378 extending vertically through the collar 362 between the superior and inferior surfaces 372, 374, the blade aperture 378 being sized and configured to receive the second retractor blade 126 therein. The superior surface 372 further includes a first threaded aperture 380 formed therein at a first oblique angle and a second threaded aperture 382 formed therein at second oblique angle. The first threaded aperture 380 is configured to receive the threaded post 392 of the adjustment post 364. The second threaded aperture 382 is configured to receive the treaded shaft 458 of the tulip connector 420. The lateral surface 376 includes a generally cylindrical recess 384 formed therein and extending in a transverse direction relative to the longitudinal axis of the blade aperture 378 such that the blade aperture 378 and recess 384 adjoin via a pass-through 386. The generally cylindrical recess 384 is sized and configured to receive at least a portion of the blade adjustment member 366 therein. The lateral surface 376 further includes a threaded aperture 388 extending from the lateral surface 376 through to the blade aperture 378. The threaded aperture 388 is sized and configured to engage the threaded shaft 414 of the lock screw 368 such that at least a portion of the threaded shaft 414 extends into the blade aperture 378 (e.g. FIG. 41). By way of example only, the threaded aperture 388 is positioned at one corner of the collar 362 and extends into the blade aperture 378 at an oblique angle relative to the transverse direction. By way of example, each of the corners and edges of the collar 362 may be rounded, chamfered, or otherwise smoothed over to reduce the impact on surrounding body tissue.

With primary reference to FIG. 30, the adjustment post 364 by way of example only includes an elongated shaft 390, a distally-extending threaded post 392, and a shaped proximal end 394. The elongated shaft 390 is sized and configured to enable manual adjustment of the angular orientation of the collar 362, and by extension the second blade 130, by acting as a lever, a handle, and an attachment point for additional torque-applying instrumentation and/or insertion handle. The threaded post 392 extends distally from the elongated shaft 390 and is configured to mate with the first threaded aperture 380 of the collar 362. The shaped proximal end 394 may have any shape or configuration that enables the proximal end 394 to mate with a suitable torque-applying instrument and/or insertion handle (not shown).

Figure 36:
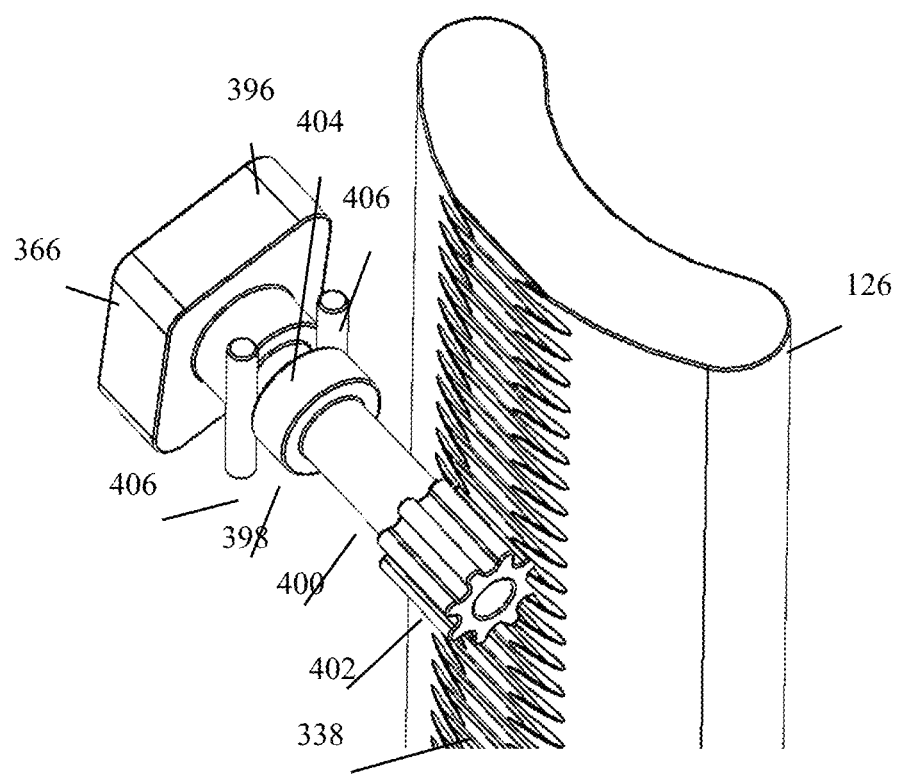
FIG. 36 is a rear perspective view of an example of a blade adjustment gear forming part of the blade holder assembly of FIG. 24 engaged with the second retractor blade of FIG. 24.
Figure 37:
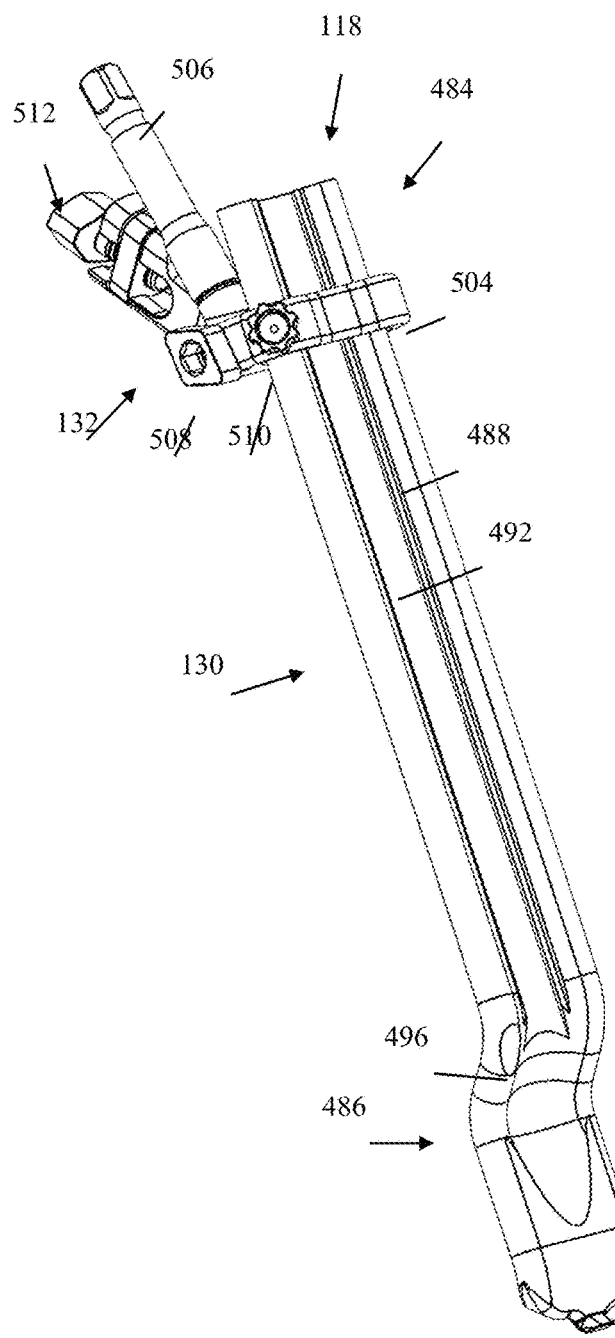
FIG. 37 is a front perspective view of a blade holder assembly coupled with a third retractor blade, forming part of the surgical retractor system of FIG. 5 according to an aspect of the disclosure.
Figure 38:
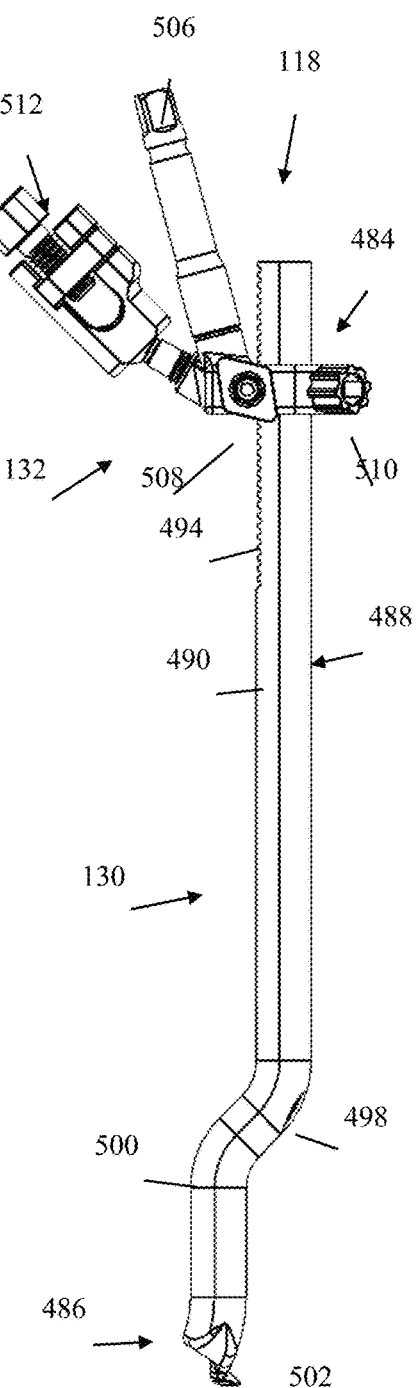
FIG. 38 is a side plan view of the blade holder assembly coupled with the third retractor blade of FIG. 37.
Figure 39:
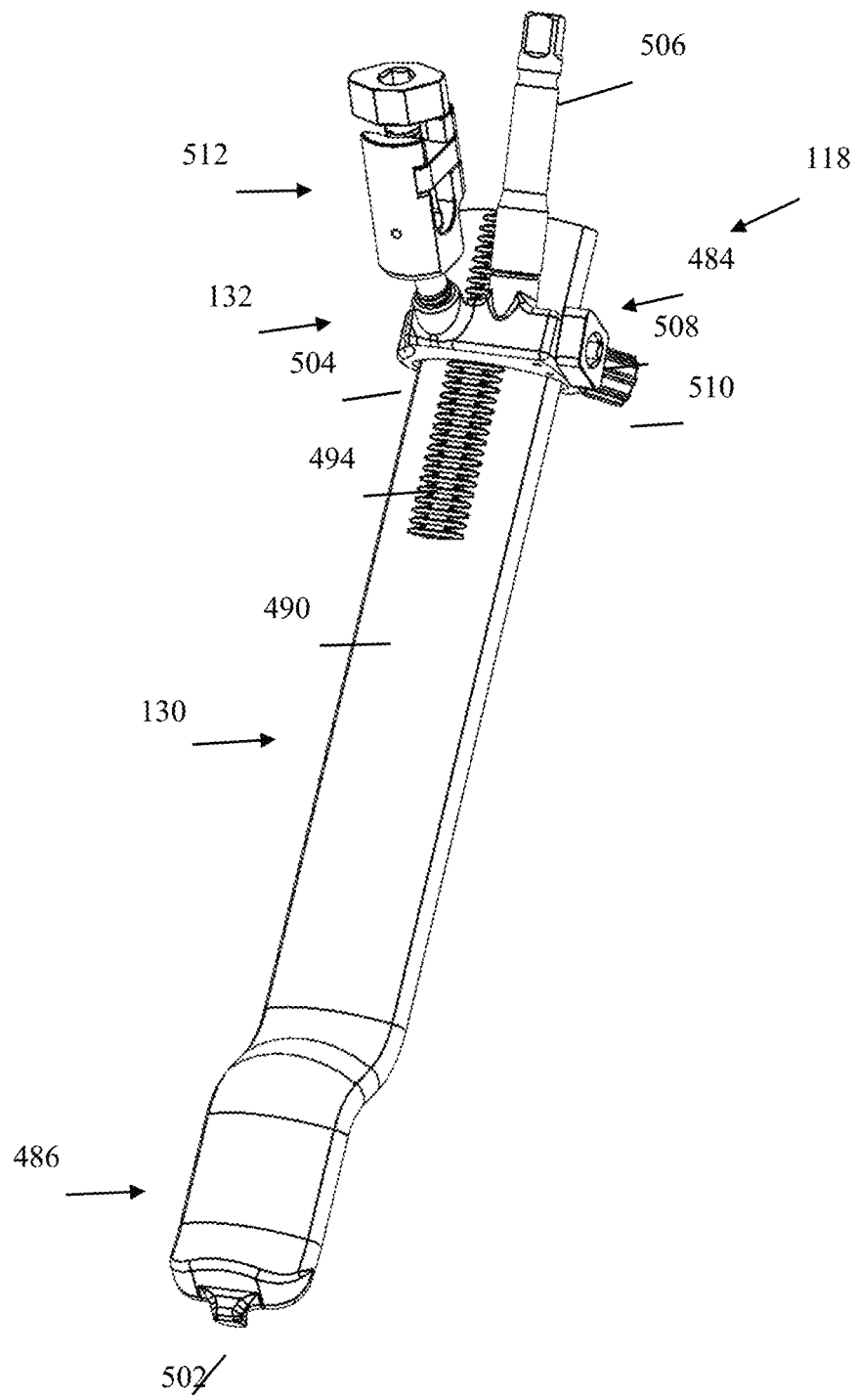
FIG. 39 is a rear perspective view of the blade holder assembly coupled with the third retractor blade of FIG. 37.
Figure 40:
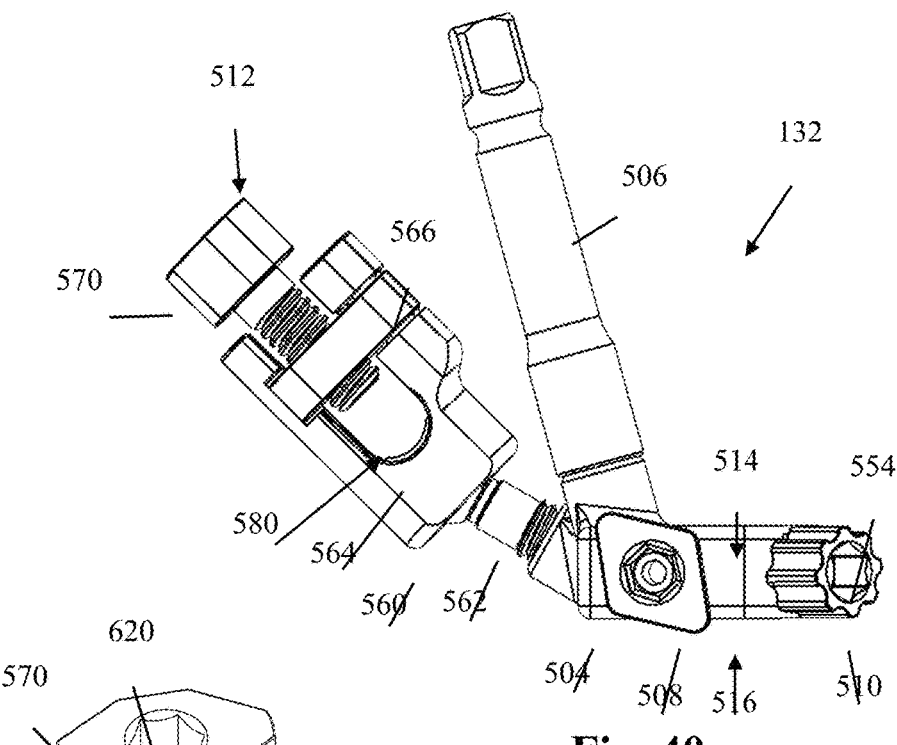
FIG. 40 is a side plan view of the blade holder assembly of FIG. 37.
Figure 41:
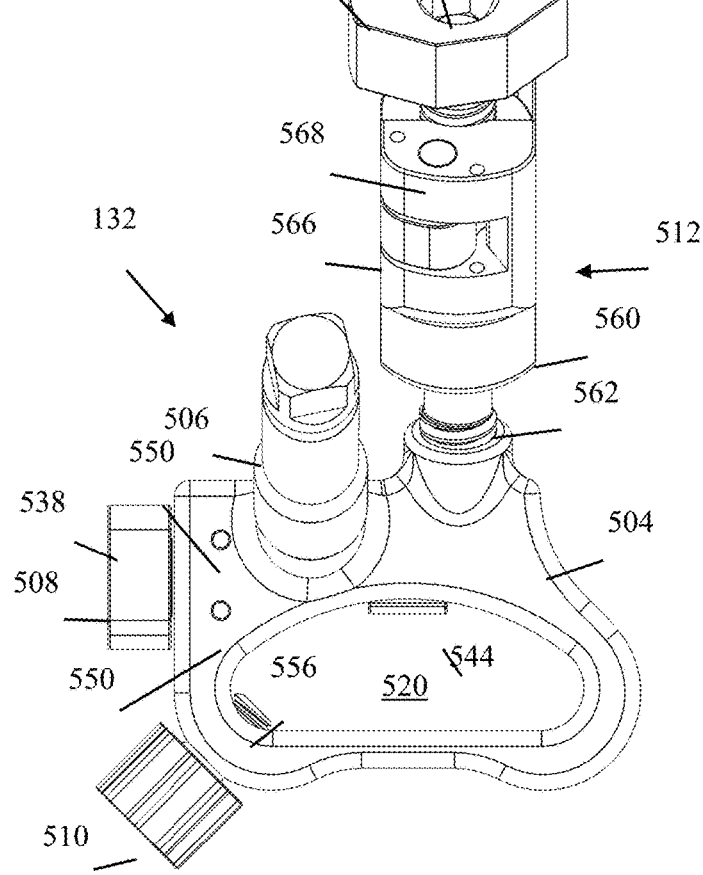
FIG. 41 is a top plan view of the blade holder assembly of FIG. 37.
Figure 42:
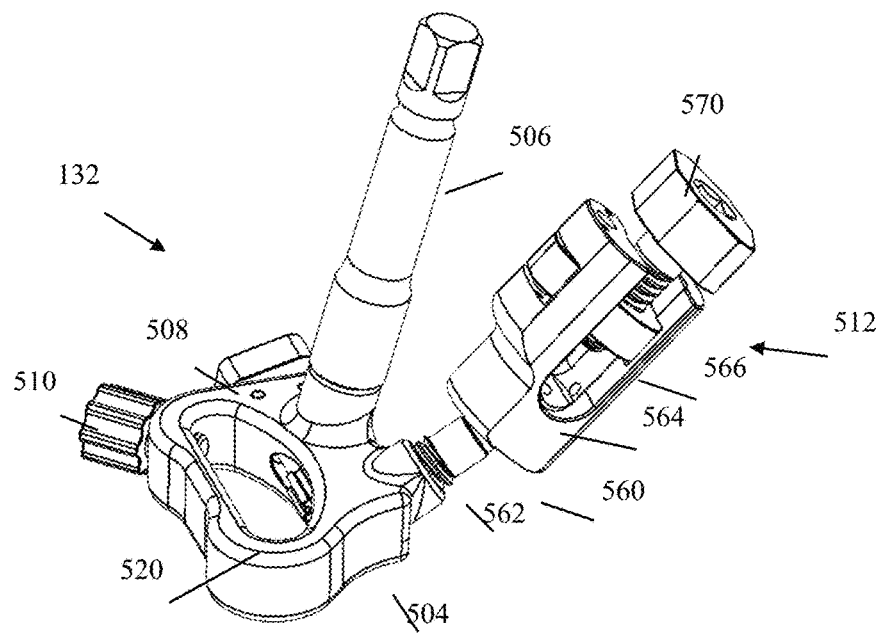
FIG. 42 is a front elevated perspective view of the blade holder assembly of FIG. 37.

By way of example, the blade adjustment member 366 comprises a head portion 396 positioned at a proximal end, a neck portion 398 positioned distally adjacent the head portion, a cylindrical shaft 400 extending distally of the neck portion, and a circular gear member 402 positioned at the distal end of the shaft 400. The head portion 396 comprises a shaped member sized and configured to be manually manipulated by a user with or without the use of additional instrumentation. The head portion 396 may have any shape suitable to enable a user to apply torque to the blade adjustment member 366, including but not limited to the diamond shape shown by way of example in FIG. 30. The neck portion 398, shaft 400, and gear member 402 are sized and configured to be received within the cylindrical recess 384 of the collar 362 such that a portion of the gear member 402 extends through the pass-through 386 into the blade aperture 378 when the blade adjustment member 366 is seated within the cylindrical recess 384 (e.g. FIG. 28). The gear member 402 engages the ridges 338 of the second retractor blade 126 when the second blade 126 is in the blade aperture 378. The engagement of the gear member 402 and ridges 338 is such that when the blade adjustment member 366 is rotated in one direction (e.g. clockwise), the second retractor blade 126 is vertically adjusted downward, and when the blade adjustment member 366 is rotated in the opposite direction (e.g. counter-clockwise), the second retractor blade 126 is vertically adjusted upward. In this manner, the length of the blade 126 that extends below the skin incision may be manually adjusted by the user. As best seen in FIG. 36, the neck portion 398 further comprises a circumferential recess 404 configured to receive at least a portion of a pair of locking pins 406 which extend through locking pin apertures 408 in the superior and inferior surfaces 372, 374 of the collar 362. The locking pins 406 prevent ejection of the blade adjustment member 366 while allowing for unencumbered rotation thereof.

The lock screw 368 has a head 410 including a driver recess 412 configured to engage a driver instrument and a threaded shaft 414 configured to threadedly engage the threaded aperture 388 of the collar 362. The head 410 further comprises a plurality of ridges 416 disposed generally parallel to the axis of the threaded shaft 414 and dispersed about the circumference of the head 410. The ridges 416 provide a frictional engagement surface for a user in the event that the lock screw 368 is hand-actuated. The distal tip of the threaded shaft 414 is configured to engage the second blade 126 when the second blade 126 is positioned within the blade aperture 378 and has been adjusted to the surgeon's preference. When the lock screw 368 is employed, the threaded shaft 414 exerts a force on the blade 126 which prevents the blade 126 from moving within the blade aperture 378 until the force has been alleviated.

With primary reference to FIGS. 30 and 33-35, the tulip assembly 370 includes a tulip 418, a tulip connector 420, a saddle 422, a swivel clamp 424, a hinge pin 426, and a tulip screw 428. By way of example only, the tulip 418 includes a base 430 and a pair of opposing first and second upstanding arms 432, 434 extending in a vertical direction away from the base 430 and separated by a distance generally corresponding to the diameter of the first retractor arm 137. The base 430 includes a pair of concave surfaces 436 disposed between the upstanding arms 432, 434 that, in combination with the upstanding arms 432, 434, form part of an arm channel 438 configured to receive the first retractor arm 137 upon final tightening of the construct. The base 430 further includes a central aperture 440 extending vertically therethrough, the central aperture 440 including a distal opening 442 through which extends the threaded shaft 458 of the tulip connector 420. The central aperture 440 further includes a generally arcuate interior surface 444 proximally adjacent the distal opening 442 and a circumferential shelf 446 proximally adjacent the arcuate interior surface 444. The generally arcuate interior surface 444 is sized and configured to receive the spherical head 454 of the tulip connector 420. The circumferential shelf 446 extends into the central aperture 440 and engages an inferior surface 464 of the saddle 422.

The first upstanding arm 432 includes a recess 448 formed therein sized and configured to receive a portion of the swivel clamp 424 therein, and a pair of axially aligned vertically-oriented pin apertures 450a, 450b positioned on either side of the recess 448 and configured to receive at least a portion of the hinge pin 426. The second upstanding arm 434 includes a recess 452 formed therein on an inner-facing side, the recess 452 sized and configured to receive a portion of the swivel clamp 424 therein.

Figure 35:
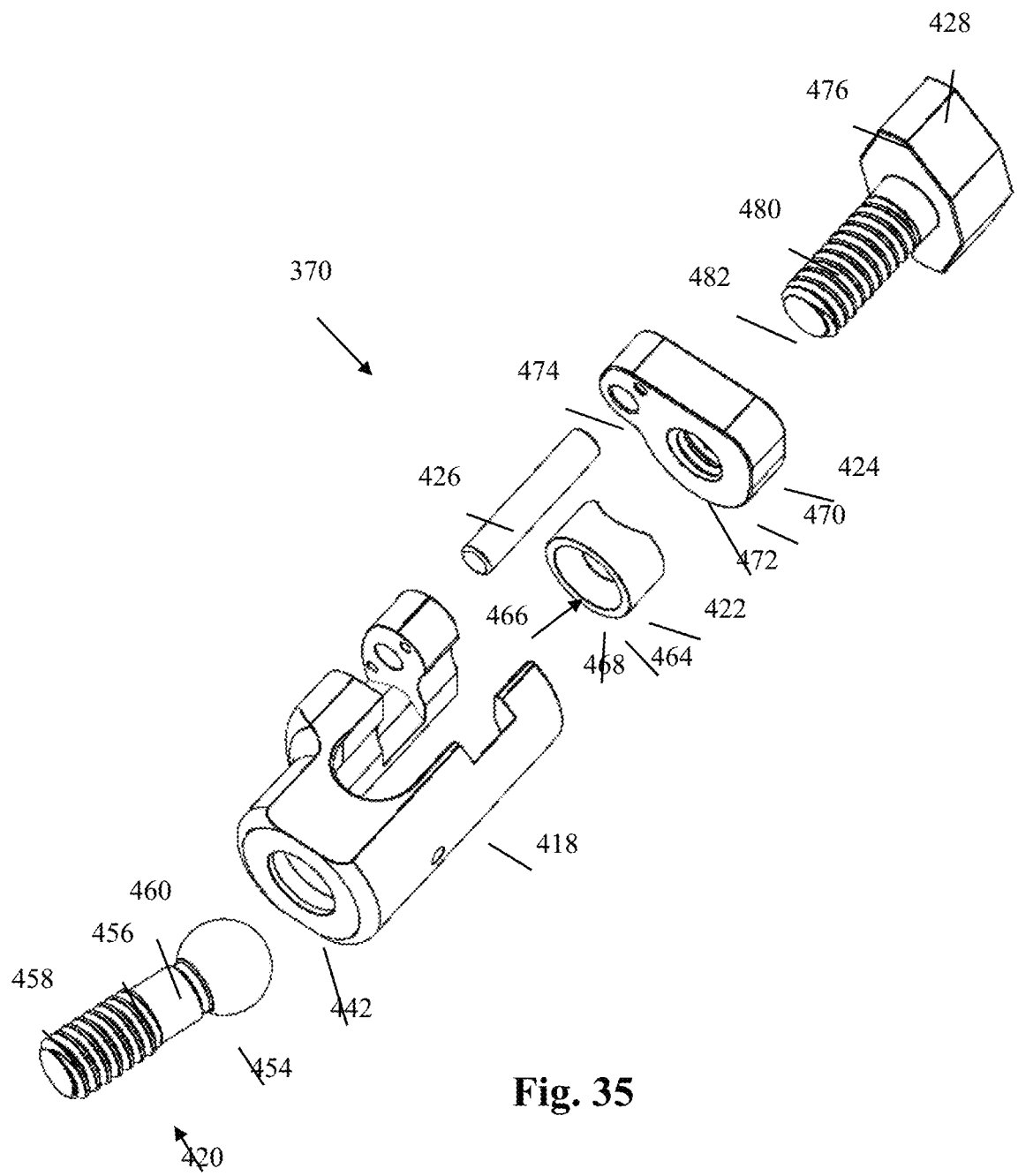
FIG. 35 is a bottom perspective view of a tulip assembly forming part of the blade holder assembly of FIG. 24.

With primary reference to FIG. 35, the tulip connector 420 includes a spherical head 454 positioned at a proximal end, and a shaft 456 extending distally from the spherical head 454, the shaft 456 including a distal threaded portion 458 and a circumferential recess 460 positioned adjacent the spherical head 454. The spherical head 454 is sized and configured to nest within the central aperture 440 of the tulip 418 while the shaft 456 extends through the distal opening 442. The distal threaded portion 458 is configured to threadedly mate with the second threaded aperture 382 of the collar 362. The interaction between the spherical head 454 and the generally arcuate interior surface 444 of the central aperture 440 enables the shaft 456 to have polyaxial pivotability in that the shaft 456 (and by extension the collar 362) is able to pivot in any direction as well as rotate about the spherical head 454 prior to final tightening of the construct. This feature ultimately allows the surgeon greater flexiblity when positioning the second retractor blade 126. The circumferential recess 460 enables the shaft 456 to have a greater pivot angle by removing material that might otherwise abut the distal opening 442.

By way of example only, the saddle 422 includes a superior surface 462 having a concave curvature, a generally planar inferior surface 464, and an inferior recess 466 having a generally arcuate surface 468. The saddle 422 is generally cylindrical and configured to nest within the central aperture 440 of the tulip 418. The superior surface 462 is configured to engage the first retractor arm 137. The inferior surface 464 is configured to engage the circumferential shelf 446, and the generally arcuate surface 468 of the inferior recess 466 is sized and configured to engage the spherical head 454 of the tulip connector 420.

The swivel clamp 424 includes a body portion 470 having a central threaded aperture 472 extending longidutionally therethrough and a hinge aperture 474 positioned toward one side of the body portion 470. The central threaded aperture 472 is sized and configured to receive at least a portion of the threaded shaft 482 of the tulip screw 428 therein. The hinge aperture 474 is sized and configured to receive the hinge pin 426 therethrough. The hinge pin 426 comprises a generally cylindrical member sized and configured such that a first end is received within the superior pin aperture 450a of the tulip 418, a second end is received within the inferior pin aperture 450b of the tulip 418, and a middle portion extends through the hinge aperture 474 of the swivel clamp 424. In this fashion, the swivel clamp 424 is hingedly coupled to the tulip 418 and capable of pivoting about the hinge pin 426. The tulip screw 428 has a head 476 including a driver recess 478 configured to engage a driver instrument and a threaded shaft 480 configured to threadedly engage the central threaded aperture 472 of the swivel clamp 424. By way of example only, the head 476 further comprises a peripheral shape providing a frictional engagement surface for a user in the event that the tulip screw 428 is hand-actuated. The distal tip 482 of the threaded shaft 480 is configured to engage the first retractor arm 137 upon final tightening of the blade holder assembly 128.

The swivel clamp 424 allows for efficient coupling (and/or uncoupling) of the second blade holder assembly 128 to the first retractor arm 137 at any time during the procedure, including but not limited to after the second retractor blade 126 has been inserted into the operative corridor. This is because the tulip screw 428 may be precoupled to the swivel clamp 424 and the swivel clamp 424 may pivot about the hinge pin 426, allowing the first retractor arm 137 to be inserted into the arm channel 438 of the tulip 418. Once the first retractor arm 137 is placed within the arm channel 438, the swivel clamp 424 is pivoted back into position acting as a crossbeam spanning between the first and second upstanding arms 432, 434 (with at least a portion of the swivel clamp 424 occupying space within each of the recesses 448, 452), thereby preventing ejection of the first retractor arm 137 from the arm channel 438. Once this occurs, and the tulip assembly 370 is positioned according to the surgeon's preferences, the tulip screw 428 may be rotated to achieve final tightening of the construct. Upon final tightening, the tulip screw 428 applies compressive force (by way of distal tip 482) on the retractor arm 137, which in turn applies the force to the saddle 422, which compresses the spherical head 454 of the tulip connector 420 against the generally arcuate surface 444 of the tulip 418, thereby locking the angle of the tulip connector 420 in place relative to the tulip 418.

FIGS. 37-49 illustrate an example of the third blade assembly 118 according to one aspect of the disclosure. With initial reference to FIGS. 37-39, and by way of example only, the third blade assembly 118 includes a third retractor blade 130 and a third blade holder assembly 132. The third retractor blade 130 may be constructed having any number of suitable features and dimensions. By way of example, the third retractor blade 130 is an elongated member having a generally rectangular peripheral shape including a length dimension and a width dimension. The third retractor blade 130 further includes a proximal end 484, a distal end 486, a first side 488, and a second side 490. During use, the proximal end 484 generally extends above the skin of a patient, the distal end 486 is positioned near the surgical target site, the first side 488 is inner-facing (e.g. facing towards the operative corridor), and the second side 490 is outer-facing (e.g. facing away from the operative corridor). The third blade 130 has a curvature in the width dimension such that the first side 488 has a generally concave curvature and the second side 490 has a generally convex curvature. The first side 488 includes one or more tracks 492 for slideably receiving surgical accessories such as a shim or light source (for example). By way of example, the first side 488 includes a single track 492 extending the longitudinal length of the third blade 130 and positioned near the middle of the first side 488. The track 492 may have any cross-sectional shape including but not limited to the dovetail shape shown best by way of example in FIG. 49. The second side 490 includes a plurality of laterally oriented ridges 494 positioned at the proximal end 484. The ridges 494 are positioned transversely relative to a longitudinal axis of the third blade 130, and are sized and configured to interact with the gear member 544 of the blade adjustment member 508. The third retractor blade 130 further includes a longitudinal aperture 496 extending the longitudinal length of the blade 130 and positioned on one side the track 492. The longitudinal aperture 496 may be sized and configured to receive therethrough a surgical accessory, for example a suction hose.

In the example shown and described herein, the third retractor blade 130 has a pair of distal curves 498, 500 that in effect laterally offset the distal end 486 relative to the proximal end 484 while maintaining the distal end 486 in a generally parallel orientation relative to the proximal end 484. The first distal curve 498 is curved toward the second side 490 and includes the distal terminus of the longitudinal aperture 496. The second distal curve 500 is curved back toward the first side 488. This enables the third blade 130 to gently engage and move anatomical structure (e.g. muscles, blood vessels, etc) away from the surgical target site as the third blade 130 is adjusted. The distal end 486 further includes a purchase element 502 extending distally therefrom which enables the distal end 486 to dock or otherwise temporarily register the distal end 486 of the third blade 130 relative to the surgical target site (e.g. by extending into the adjacent vertebral bodies and/or the disc space). For example, during a retroperitoneal surgical approach to the L5-S1 disc space, the purchase element 502 may dock to the sacrum, and remain docked for the duration of the procedure. This advantageously maintains the barrier between the surgical target site and the surrounding vasculature. By way of example, the purchase element 502 may be any structure suitable for achieving purchase in bone (or disc space registration), including but not limited to a tack, wedge, pin, screw, and nail.

Figure 44:
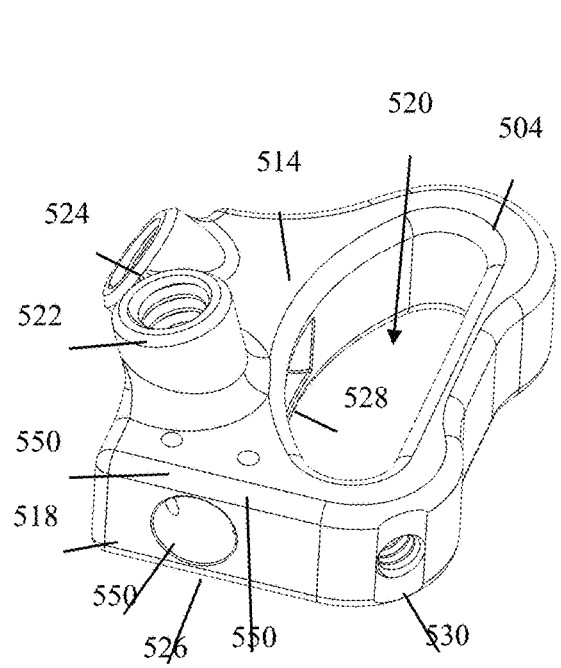
FIG. 44 is an elevated perspective view of an example of a blade holder forming part of the blade holder assembly of FIG. 37.
Figure 45:
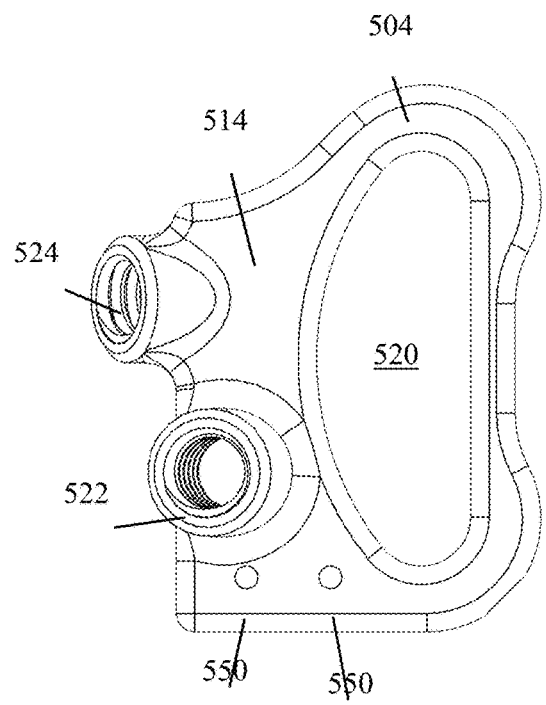
FIG. 45 is a top plan view of the blade holder of FIG. 44.

The third blade holder assembly 132 includes a collar 504, an adjustment post 506, a blade adjustment member 508, a lock screw 510, and a tulip assembly 512. With reference to FIGS. 44-45, the collar 504 includes a superior surface 514, inferior surface 516, and a lateral surface 518 extending around the periphery of the collar 504 between the superior surface 514 and inferior surface 516. The collar 504 further includes a blade aperture 520 extending vertically through the collar 504 between the superior and inferior surfaces 514, 516, the blade aperture 520 being sized and configured to receive the third retractor blade 130 therein. The superior surface 514 further includes first threaded aperture 522 formed therein at a first oblique angle and a second threaded aperture 524 formed therein at second oblique angle. The first threaded aperture 522 is configured to receive the threaded post 534 of the adjustment post 506. The second threaded aperture 524 is configured to receive the treaded shaft 600 of the tulip connector 562. The lateral surface 518 includes a generally cylindrical recess 526 formed therein and extending in a transverse direction relative to the longitudinal axis of the blade aperture 520 such that the blade aperture 520 and recess 526 adjoin via a pass-through 528. The generally cylindrical recess 526 is sized and configured to receive at least a portion of the blade adjustment member 508 therein. The lateral surface 518 further includes a threaded aperture 530 extending from the lateral surface 518 through to the blade aperture 520. The threaded aperture 530 is sized and configured to engage the threaded shaft 556 of the lock screw 510 such that at least a portion of the threaded shaft 556 extends into the blade aperture 520 (e.g. FIG. 41). By way of example only, the threaded aperture 530 is positioned at one corner of the collar 504 and extends into the blade aperture 520 at an oblique angle relative to the transverse direction. By way of example, each of the corners and edges of the collar 504 may be rounded, chamfered, or otherwise smoothed over to reduce the impact on surrounding body tissue.

Figure 43:
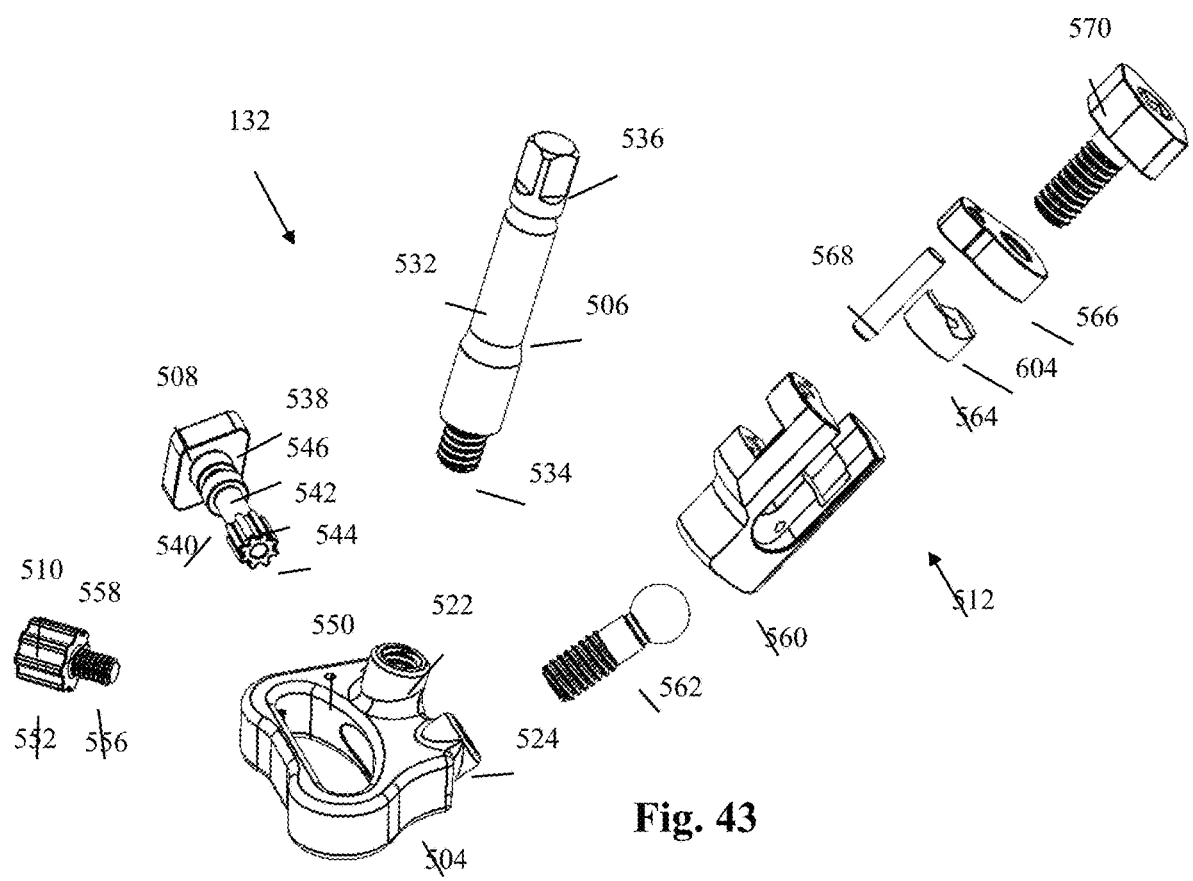
FIG. 43 is a front elevated exploded perspective view of the blade holder assembly of FIG. 37.

With primary reference to FIG. 43, the adjustment post 506 by way of example only includes an elongated shaft 532, a distally-extending threaded post 534, and a shaped proximal end 536. The elongated shaft 532 is sized and configured to enable manual adjustment of the angular orientation of the collar 504, and by extension the third blade 130, by acting as a lever, a handle, and an attachment point for additional torque-applying instrumentation and/or insertion handle. The threaded post 534 extends distally from the elongated shaft 532 and is configured to mate with the threaded aperture 522 of the collar 504. The shaped proximal end 536 may have any shape or configuration that enables the proximal end 536 to mate with a suitable torque-applying instrument and/or insertion handle (not shown).

By way of example, the blade adjustment member 508 comprises a head portion 538 positioned at a proximal end, a neck portion 540 positioned distally adjacent the head portion, a cylindrical shaft 542 extending distally of the neck portion, and a circular gear member 544 positioned at the distal end of the shaft 542. The head portion 538 comprises a shaped member sized and configured to be manually manipulated by a user with or without the use of additional instrumentation. The head portion 538 may have any shape suitable to enable a user to apply torque to the blade adjustment member 508, including but not limited to the diamond shape shown by way of example in FIG. 40. The neck portion 540, shaft 542, and gear member 544 are sized and configured to be received within the cylindrical recess 526 of the collar 504 such that a portion of the gear member 544 extends through the pass-through 528 into the blade aperture 520 when the blade adjustment member 508 is seated within the cylindrical recess 526 (e.g. FIG. 41). The gear member 544 engages the ridges 494 of the third retractor blade 130 when the third blade 130 is in the blade aperture 520. The engagement of the gear member 544 and ridges 494 is such that when the blade adjustment member 508 is rotated in one direction (e.g. clockwise), the third retractor blade 130 is vertically adjusted downward, and when the blade adjustment member 508 is rotated in the opposite direction (e.g. counter-clockwise), the third retractor blade 130 is vertically adjusted upward. In this manner, the length of the blade 130 that extends below the skin incision may be manually adjusted by the user. The neck portion 540 further comprises a circumferential recess 546 configured to receive at least a portion of a pair of locking pins 548 which extend through locking pin apertures 550 in the superior and inferior surfaces 514, 516 of the collar 504. The locking pins 548 prevent ejection of the blade adjustment member 508 while allowing for unencumbered rotation thereof.

The lock screw 510 has a head 552 including a driver recess 554 configured to engage a driver instrument and a threaded shaft 556 configured to threadedly engage the threaded aperture 530 of the collar 504. The head 552 further comprises a plurality of ridges 558 disposed generally parallel to the axis of the threaded shaft 556 and dispersed about the circumference of the head 552. The ridges 558 provide a frictional engagement surface for a user in the event that the lock screw 510 is hand-acutated. The distal tip of the threaded shaft 556 is configured to engage the third blade 130 when the third blade 130 is positioned within the blade aperture 520 and has been adjusted to the surgeon's preference. When the lock screw 510 is employed, the threaded shaft 556 exerts a force on the blade 130 which prevents the blade 130 from moving within the blade aperture 520 until the force has been alleviated.

Figure 46:
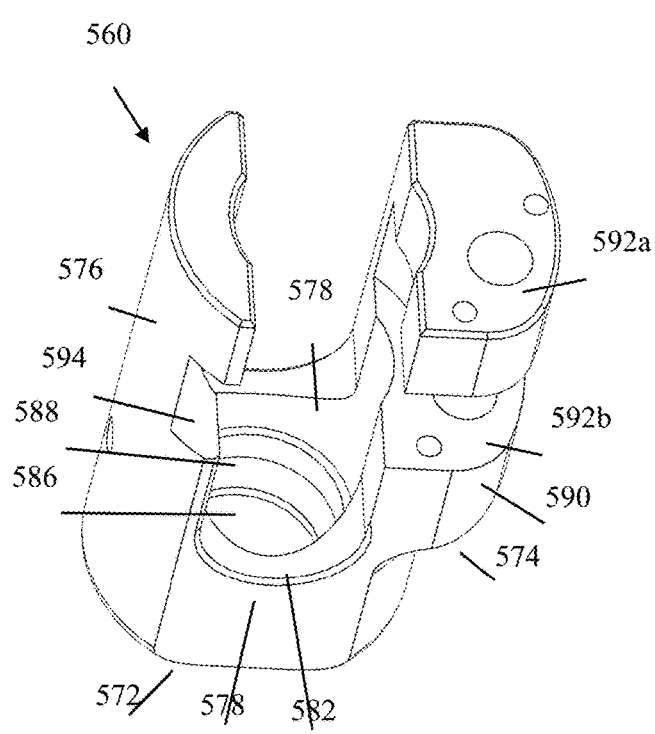
FIG. 46 is an elevated perspective view of a tulip forming part of the blade holder assembly of FIG. 37.
Figure 47:
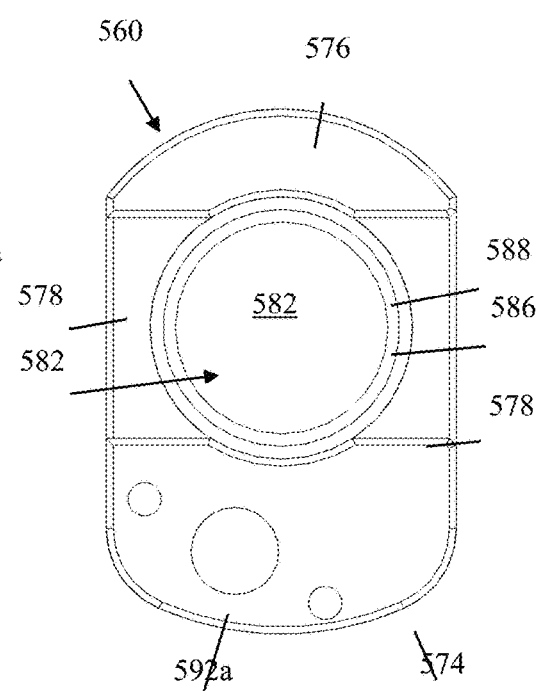
FIG. 47 is a top plan view of the tulip of FIG. 45.
Figure 48:
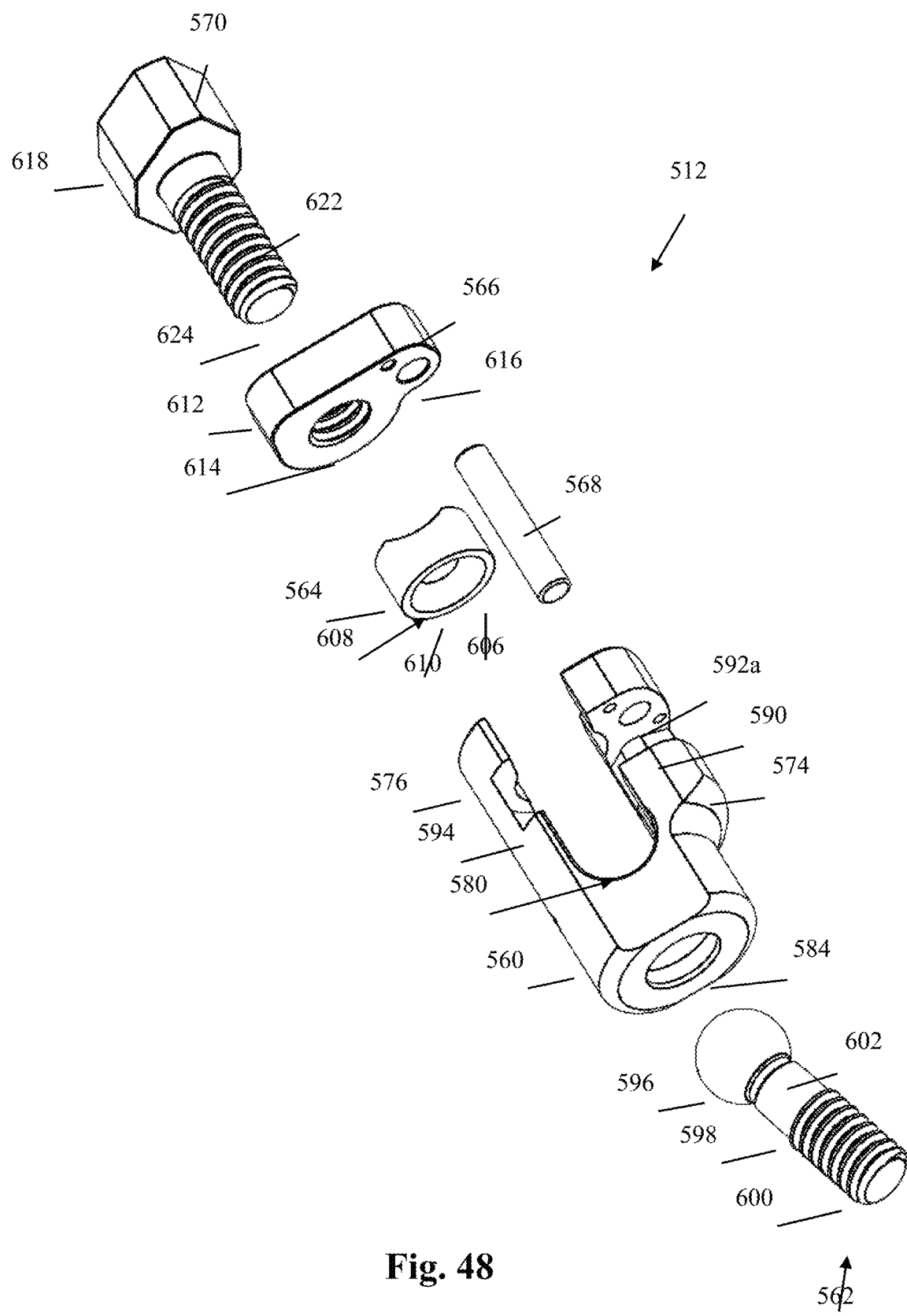
FIG. 48 is a bottom perspective view of a tulip assembly forming part of the blade holder assembly of FIG. 37.
Figure 49:
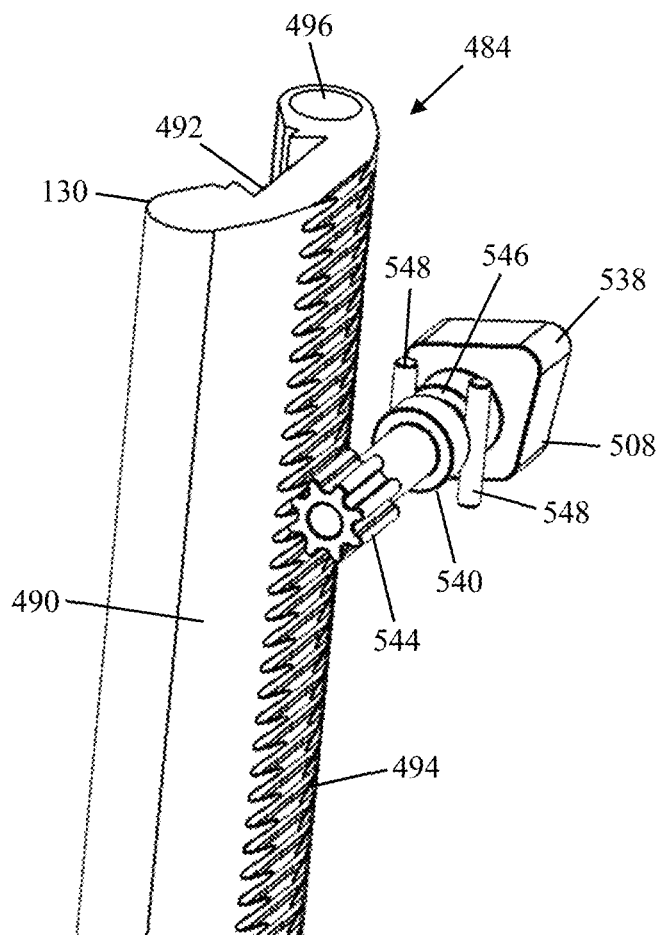
FIG. 49 is a rear perspective view of an example of a blade adjustment gear forming part of the blade holder assembly of FIG. 37 engaged with the third retractor blade of FIG. 37.

With primary reference to FIGS. 43 and 46-47, the tulip assembly 512 includes a tulip 560, a tulip connector 562, a saddle 564, a swivel clamp 566, a hinge pin 568, and a tulip screw 570. By way of example only, the tulip 560 includes a base 572 and a pair of opposing first and second upstanding arms 574, 576 extending in a vertical direction away from the base 572 and separated by a distance generally corresponding to the diameter of the second retractor arm 139. The base 572 includes a pair of concave surfaces 578 disposed between the upstanding arms 574, 576 that, in combination with the upstanding arms 574, 576, form part of an arm channel 580 configured to receive the second retractor arm 139 upon final tightening of the construct. The base 572 further includes a central aperture 582 extending vertically therethrough, the central aperture 582 including a distal opening 584 through which extends the threaded shaft 600 of the tulip connector 562. The central aperture 582 further includes a generally arcuate interior surface 586 proximally adjacent the distal opening 584 and a circumferential shelf 588 proximally adjacent the arcuate interior surface 586. The generally arcuate interior surface 586 is sized and configured to receive the spherical head 596 of the tulip connector 562. The circumferential shelf 588 extends into the central aperture 582 and engages an inferior surface 606 of the saddle 564.

The first upstanding arm 574 includes a recess 590 formed therein sized and configured to receive a portion of the swivel clamp 566 therein, and a pair of axially aligned vertically-oriented pin apertures 592a, 592b positioned on either side of the recess 590 and configured to receive at least a portion of the hinge pin 568. The second upstanding arm 576 includes a recess 594 formed therein on an inner-facing side, the recess 594 sized and configured to receive a portion of the swivel clamp 566 therein.

The tulip connector 562 includes a spherical head 596 positioned at a proximal end, and a shaft 598 extending distally from the spherical head 596, the shaft 598 including a distal threaded portion 600 and a circumferential recess 602 positioned adjacent the spherical head 596. The spherical head 596 is sized and configured to nest within the central aperture 582 of the tulip 560 while the shaft 598 extends through the distal opening 584. The distal threaded portion 600 is configured to threadedly mate with the second threaded aperture 524 of the collar 504. The interaction between the spherical head 596 and the generally arcuate interior surface 586 of the central aperture 582 enables the shaft 598 to have polyaxial pivotability in that the shaft 598 (and by extension the collar 504) is able to pivot in any direction as well as rotate about the spherical head 596 prior to final tightening of the construct. This feature ultimately allows the surgeon greater flexiblity when positioning the third retractor blade 130. The circumferential recess 602 enables the shaft 598 to have a greater pivot angle by removing material that might otherwise abut the distal opening 584.

By way of example only, the saddle 564 includes a superior surface 604 having a concave curvature, a generally planar inferior surface 606, and an inferior recess 608 having a generally arcuate surface 610. The saddle 564 is generally cylindrical and configured to nest within the central aperture 582 of the tulip 560. The superior surface 604 is configured to engage the second retractor arm 139. The inferior surface 606 is configured to engage the circumferential shelf 588, and the generally arcuate surface 610 of the inferior recess 608 is sized and configured to engage the spherical head 596 of the tulip connector 562.

The swivel clamp 566 includes a body portion 612 having a central threaded aperture 614 extending longidutionally therethrough and a hinge aperture 616 positioned toward one side of the main body portion 612. The central threaded aperture 614 is sized and configured to receive at least a portion of the threaded shaft 622 of the tulip screw 570 therein. The hinge aperture 616 is sized and configured to receive the hinge pin 568 therethrough. The hinge pin 568 comprises a generally cylindrical member sized and configured such that a first end is received within the superior pin aperture 592a of the tulip 560, a second end is received within the inferior pin aperture 592b of the tulip 560, and a middle portion extends through the hinge aperture 616 of the swivel clamp 566. In this fashion, the swivel clamp 566 is hingedly coupled to the tulip 560 and capable of pivoting about the hinge pin 568. The tulip screw 570 has a head 618 including a driver recess 620 configured to engage a driver instrument and a threaded shaft 622 configured to threadedly engage the central threaded aperture 614 of the swivel clamp 566. By way of example only, the head 618 further comprises a peripheral shape providing a frictional engagement surface for a user in the event that the tulip screw 570 is hand-acutated. The distal tip 624 of the threaded shaft 622 is configured to engage the first retractor arm 137 upon final tightening of the blade holder assembly 132.

The swivel clamp 566 allows for efficient coupling (and/or uncoupling) of the third blade holder assembly 132 to the second retractor arm 139 at any time during the procedure, including but not limited to after the third retractor blade 130 has been inserted into the operative corridor. This is because the tulip screw 570 may be precoupled to the swivel clamp 566 and the swivel clamp 566 may pivot about the hinge pin 568, allowing the second retractor arm 139 to be inserted into the arm channel 580 of the tulip 560. Once the second retractor arm 139 is placed within the arm channel 580, the swivel clamp 566 is pivoted back into position acting as a crossbeam spanning between the first and second upstanding arms 574, 576 (with at least a portion of the swivel clamp 566 occupying space within each of the recesses 590, 594), thereby preventing ejection of the second retractor arm 139 from the arm channel 580. Once this occurs, and the tulip assembly 512 is positioned according to the surgeon's preferences, the tulip screw 570 may be rotated to achieve final tightening of the construct. Upon final tighening, the tulip screw 570 applies compressive force (by way of distal tip 624) on the retractor arm 139, which in turn applies the force to the saddle 564, which compresses the spherical head 596 of the tulip connector 562 against the generally arcuate surface 586 of the tulip 560, thereby locking the angle of the tulip connector 562 in place relative to the tulip 560.

The retractor systems 10, 110 may be used according to the methodologies set forth in U.S. Pat. No. 9,451,940 forming part of this disclosure. More specifically, the retractor systems 10, 110 may be used during any number of described surgical approaches to the spine of a patient, including but not limited to a minimally invasive retroperitoneal approach to the L5-S1 disc space in order to perform a spinal fusion procedure. During such a procedure, any number of suitable implants and instrumentation may be used, including but not limited to those set forth in U.S. Pat. No. 9,451,940.

Figure 50:
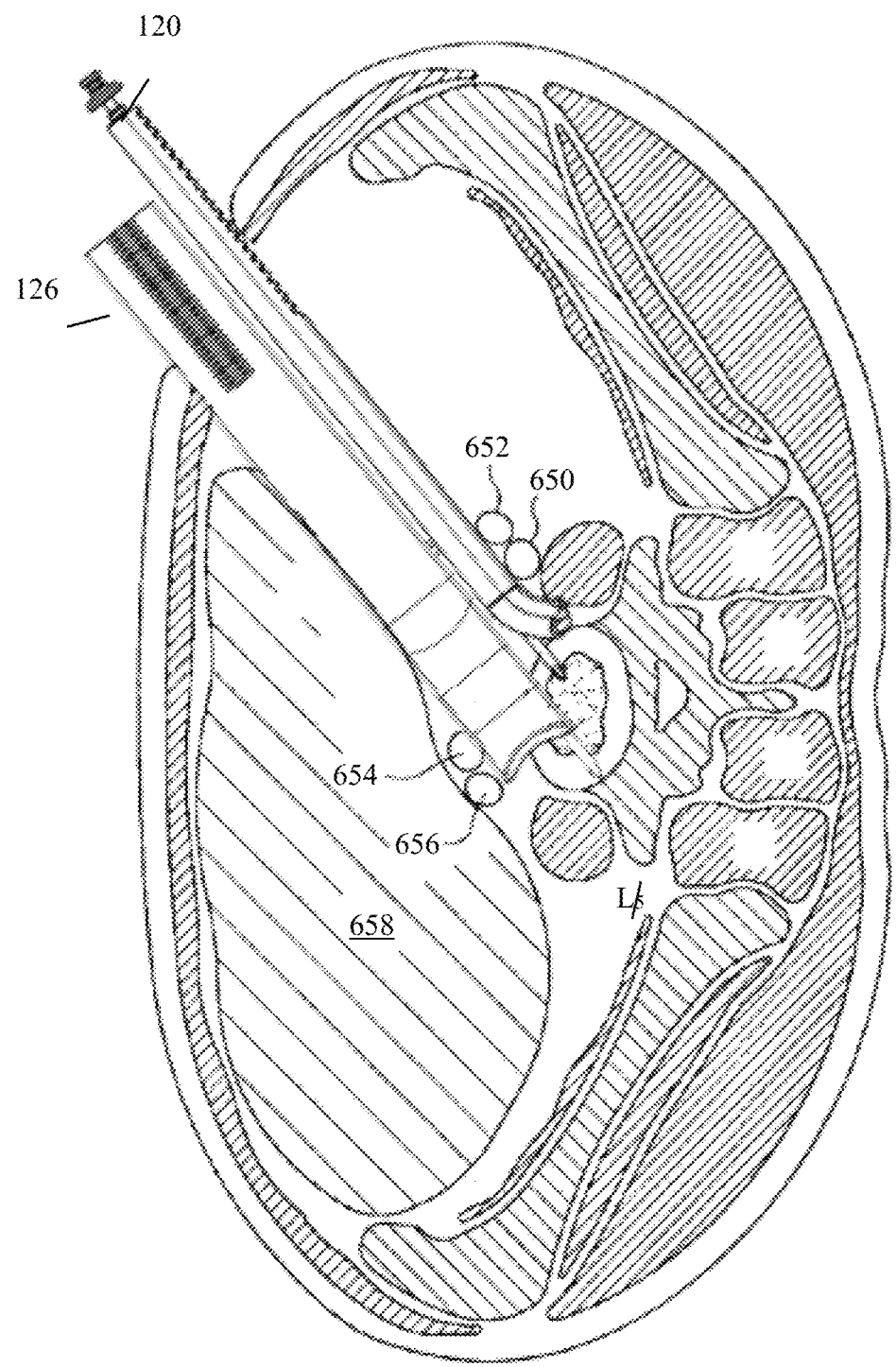
FIG. 50 is a schematic cross-sectional view of the abdomen at the level of the L5-S1 intervertebral space illustrating left anterolateral displacement of the peritoneum and the right anterolateral introduction of first and second blades of the surgical retractor system of FIG. 5, with the right and left iliac vessels retracted away from the anterior spine.

For example, during a retroperitoneal approach (e.g. such as described in U.S. Pat. No. 9,451,940), the retractor 110 provides mechanical protection to arteries and vessels that go to the legs. More specifically, the retractor 110 may be positioned below the bifurcation of iliac arteries and vessels in order to first displace the vessels and arteries to provide exposure to the L5-S1 disc space, and then shield the vessels and arteries from damage during the procedure. The retractor 110 of the present disclosure is employed after the surgeon has established initial access to the surgical target site (e.g. L5-S1 disc space) via finger dissection and/or dilation. By way of example, when the retractor 110 is initially introduced, only the first retractor blade 120 may be coupled to the retractor body 112 as described above. The retractor arms 137, 139 are not initialy associated with either the second or third blade assemblies 116, 118, and may be pivoted and/or rotated away from the surgical site so as to be out of the way of activity in and around the surgical incision. The first retractor blade 120 (coupled with the retractor body 112) is inserted through the operative corridor until the distal end is near the L5 vertebra. Caution is used to first avoid surrounding vasculature such as iliac arteries 650 and veins 652 during insertion of the blade 120, and to use the blade to engage and displace the arteries and veins from the operative corridor. When the first blade 120 is in position, an anchor pin 268 may be used to dock the first blade 120 to the L5 vertebra, as shown by way of example in FIG. 50. At this point (or before this point), the retractor body 112 may be coupled to the patient's bed via an articulating arm (not shown) so that the retractor has stability in being secured to both the patient and the patient's bed.

Once the first blade 120 is in position, the second blade 126 may be employed in a similar fashion to the first blade 120. The second blade 126 may be initially coupled to the second blade holder assembly 128. The second blade 126 is then introduced into the operative corridor until the distal end is near the surgical target site. The blade 126 is then used to engage and displace surrounding arteries 654 and veins 656 from the operative corridor, creating access to the L5-S1 disc space. The second blade 126 may then be coupled to the first retractor arm 137 as described above. Additionally, an anchor pin may be used to dock the second blade 126 to the L5 vertebra, as shown by way of example in FIG. 50.

Once the second blade 126 is in position, the third blade 130 may be employed in a nearly identical fashion to the second blade 126. The third blade 130 may be initially coupled to the third blade holder assembly 132. The third blade 130 is then introduced into the operative corridor until the distal end is positioned near the surgical target site. The blade 130 may then be used to engage and displace any surrounding tissue, for example the peritoneum 658. The blade 130 may be docked to the sacrum using the purchase element 502 at the distal tip of the blade 130. Thus at this point, all three retractor blades 120, 126, 128 are registered to bony structure within the patient and the retractor body 112 is secured to the patient's bed, which establishes a secure operative corridor that does not constantly need to be monitored or maintained by human hands. Once the operative corridor has been established providing safe access to the surgical target site (e.g. L5-S1 disc space), the surgical procedure may proceed.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of any claims based on this disclosure.

Any of the features or attributes of the above the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by any claims based on this disclosure when interpreted in accordance with the benefit to which they are fairly, legally, and equitably entitled.

What is claimed is:

1. A surgical retractor system, comprising:
   a retractor body having a proximal end, a distal end, and a longitudinal axis extending through the proximal and distal ends, the retractor body having at least one articulation joint along the longitudinal axis and a pair of opposing first and second arm extensions pivotably coupled thereto;
   a first blade assembly including a first retractor blade and a first collar, the first collar being integrally formed with the retractor body and positioned along the longitudinal axis at the distal end, the first collar configured to couple with the first retractor blade;
   a second blade assembly removably coupled to the first arm extension, the second blade assembly including a second retractor blade and a blade holder assembly, the blade holder assembly of the second blade assembly including a second collar removably coupled to the first arm extension by a first polyaxial joint spaced apart from the second collar; and
   a third blade assembly removably coupled to the second arm extension, the third blade assembly including: a third retractor blade having a distal purchase protrusion integrally formed with and extending distally from a distal end of the third retractor blade such that the distal end of the third retractor blade is shaped differently from a distal end of the second retractor blade, and a blade holder assembly, the blade holder assembly of the third blade assembly including a third collar removably coupled to the second arm extension by a polyaxial joint spaced apart from the third collar.

2. The system of claim 1, wherein the first blade assembly further includes a first height adjustment actuator, the first height adjustment actuator being movable relative to the first retractor blade to cause the first retractor blade to translate vertically within the first collar.

3. The system of claim 2, wherein the first blade assembly further includes an anchor pin coupled with the first retractor blade, the anchor pin having a distal tip configured to gain purchase within bone.

4. The system of claim 2, wherein the second blade assembly further includes a second height adjustment actuator, the second height adjustment actuator being movable relative to the second retractor blade to cause the second retractor blade to translate vertically within the second collar.

5. The system of claim 4, wherein the second blade assembly further includes an anchor pin coupled with the second retractor blade, the anchor pin having a distal tip configured to gain purchase within bone.

6. The system of claim 4, wherein the third blade assembly further includes a third height adjustment actuator, the third height adjustment actuator being movable relative to the third retractor blade to cause the third retractor blade to translate vertically within the third collar.

7. The system of claim 1, wherein the second blade assembly further comprises a coupling element positioned between the second collar and the first arm extension, the coupling element including a receptacle for receiving therein at least a portion of the first arm extension and a hinged barrier moveable from a first position permitting at least one of ingress and egress into the receptacle to a second position preventing ingress and egress into the receptacle.

8. The system of claim 7, wherein the hinged barrier further comprises a lock.

9. The system of claim 8, wherein the lock is configured to:

lock the hinged barrier in a closed configuration; and lock the first polyaxial joint in a selected angular orientation.

10. The system of claim 1, wherein the distal purchase protrusion integrally formed with the third retractor blade is configured to dock to a sacrum bone.

11. The system of claim 1, wherein the third blade assembly further comprises a coupling element positioned between the third collar and the second arm extension, the coupling element including a receptacle for receiving therein at least a portion of the second arm extension and a hinged barrier moveable from a first position permitting at least one of ingress and egress into the receptacle to a second position preventing ingress and egress into the receptacle.

12. The system of claim 11, wherein the hinged barrier further comprises a lock.

13. The system of claim 12, wherein the lock is configured to:

lock the hinged barrier in a closed configuration; and lock the second polyaxial joint in a selected angular orientation.

14. The system of claim 1, wherein the second retractor blade comprises an elongated element having a proximal end, a distal end, an interior face oriented toward the third retractor blade, and at least a longitudinal convex curvature and longitudinal concave curvature in the interior face such that the interior face at the distal end of the second retractor blade is laterally offset from the proximal end in a direction toward the third retractor blade.

15. The system of claim 14, wherein the third retractor blade comprises an elongated element having a proximal end, a distal end, an interior face oriented toward the second retractor blade, and at least a longitudinal convex curvature and longitudinal concave curvature such that the interior face at the distal end of the third retractor blade is laterally offset from the proximal end in a direction away from the second retractor blade.

16. The system of claim 15, wherein the first retractor blade comprises an elongate element having a proximal end, a distal end, a width, an exterior face oriented away from the second and third retractor blades, and interior face opposite from the exterior face, wherein the exterior face includes a longitudinal concave curvature and the interior face includes a generally longitudinal convex curvature.

17. The system of claim 16, wherein the first retractor blade is curved away from the second and third retractor blades at the distal end of the first retractor blade.

18. The system of claim 1, wherein the first retractor blade comprises one or more tracks for slidably receiving surgical accessories.

19. The system of claim 1, wherein the second blade assembly further comprises a tulip assembly configured to cause movement of the second retractor blade for positioning.

20. The system of claim 1, wherein the third blade assembly further comprises a tulip assembly configured to cause movement of the third retractor blade for positioning.

* * * * *

UNITED STATES PATENT AND TRADEMARK OFFICE
CERTIFICATE OF CORRECTION

PATENT NO. : 10,716,553 B2
APPLICATION NO. : 15/956455
DATED : July 21, 2020
INVENTOR(S) : Scott Spann et al.

Page 1 of 1

It is certified that error appears in the above-identified patent and that said Letters Patent is hereby corrected as shown below:

In the Claims

Column 26, Line 15: In Claim 16, delete "generally".

Signed and Sealed this
Third Day of November, 2020

Andrei Iancu
*Director of the United States Patent and Trademark Office*